(12) United States Patent
Tsai et al.

(10) Patent No.: US 10,328,042 B2
(45) Date of Patent: *Jun. 25, 2019

(54) CO-CRYSTALS OF SUBSTITUTED GLYCINE AND USES THEREOF

(71) Applicant: SyneuRx International (Taiwan) Corp., New Taipei (TW)

(72) Inventors: Guochuan Emil Tsai, Pasadena, CA (US); Ching-Cheng Wang, New Taipei (TW); Tien-Lan Hsieh, New Taipei (TW)

(73) Assignee: SyneuRx International (Taiwan) Corp., New Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/944,722

(22) Filed: Apr. 3, 2018

(65) Prior Publication Data

US 2018/0228754 A1   Aug. 16, 2018

Related U.S. Application Data

(60) Division of application No. 15/866,303, filed on Jan. 9, 2018, which is a continuation of application No. 15/430,750, filed on Feb. 13, 2017, now Pat. No. 9,877,942.

(51) Int. Cl.
| | | |
|---|---|---|
| *A61K 31/198* | (2006.01) | |
| *A61K 47/12* | (2006.01) | |
| *C07C 229/12* | (2006.01) | |
| *C07C 59/255* | (2006.01) | |
| *C07C 57/15* | (2006.01) | |
| *C07D 307/62* | (2006.01) | |

(52) U.S. Cl.
CPC ............ *A61K 31/198* (2013.01); *A61K 47/12* (2013.01); *C07C 57/15* (2013.01); *C07C 59/255* (2013.01); *C07C 229/12* (2013.01); *C07D 307/62* (2013.01); *C07B 2200/13* (2013.01)

(58) Field of Classification Search
CPC .................................................. A61K 31/198
USPC ......................................................... 514/561
See application file for complete search history.

(56) References Cited

U.S. PATENT DOCUMENTS 9,877,942 B1   1/2018 Tsai et al.

FOREIGN PATENT DOCUMENTS

WO   WO 2008/153945 A2   12/2008
WO   WO 2016/001681 A1   1/2016

OTHER PUBLICATIONS

Shaheen et al., Frontiers in Psychiatry (2013), vol. 4(52), pp. 1-7.*
Hai et al., Neuropharmacol. (2009), vol. 57, pp. 551-555.*
By Fleck et al., J. Mol. Structure, (2013), vol. 1045, pp. 95-103. Filed by applicant in parent U.S. Appl. No. 15/430,750.*
Yadav et al., Indian J. Pharm. Sci. (2009) vol. 71(4), pp. 359-370.*
Regulatory Classification of Pharmaceutical Co-Crystals, FDA, Guidance for Industry (2016), pp. 1-7.*
Sun et al., J. Chem. and Eng. Data, 2015, 60, 1166-1172. submitted in U.S. Appl. No. 15/866,303.*
Fukte et al., Conformer selection: an important tool in cocrystal formation. Int J Pharma Pharmc Sciences. 2014;6(7):9-14.
Losev et al., Polymorphic transformations in glycine co-crystals at low temperate and high pressure: two new examples as a follow-up to a glycine-glutaric acid study. CrystEngComm. 2016;18:5869.
Losev et al., The effect of carboxylic acids on glycine polymorphism, salt and co-crystal formation. A comparison of different crystallization techniques. New J Chem. 2013;37:1973.
Ong, Crystal engineering of molecular and ionic cocrystals. Graduate theses and dissertation. University of South Florida. Mar. 25, 2011. 1-193.
Wang et al., Co-crystallization of glycine anhydride with the hydroxybenzoic acids: controlled formation of dimers via synthons cooperation and structural characterization. Science China. Nov. 2012;55(11):2381-2387.

* cited by examiner

*Primary Examiner* — Taofiq A Solola
(74) *Attorney, Agent, or Firm* — Polsinelli

(57) ABSTRACT

The present disclosure provides co-crystals of a substituted glycine compound and a co-former compound of Formula (I):

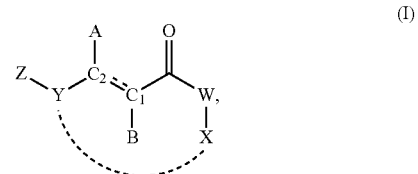

compositions comprising such, and uses thereof in treating and/or reducing the risk for a neuropsychiatric disorder (e.g., schizophrenia, psychotic disorders, depressive disorders, suicidal ideation and/or behavior, obsessive compulsive disorder or Alzheimer's disease). Also provided herein are methods for preparing the co-crystals.

20 Claims, 23 Drawing Sheets

B.

A.

CO-CRYSTALS OF SUBSTITUTED GLYCINE AND USES THEREOF

RELATED APPLICATIONS

This application is a divisional of and claims priority under 35 U.S.C. § 120 to U.S. Application, U.S. Ser. No. 15/866,303, filed Jan. 9, 2018, which is a continuation of and claims priority under 35 U.S.C. § 120 to U.S. application Ser. No. 15/430,750, filed Feb. 13, 2017, now U.S. Pat. No. 9,877,942. Each of the prior applications is incorporated by reference herein in its entirety.

BACKGROUND OF THE INVENTION

Co-crystals are a homogeneous multicomponent system including at least one drug substance (i.e., active ingredient) and at least one co-former, which are held together by supramolecular synthons. Pharmaceutical co-crystals have attracted significant interest due to the co-crystals' contribution to potential advantageous physicochemical properties of the drug substance, for example, improved solubility, dissolution rate, bioavailability, physical and/or chemical stability, flowability, hygroscopicity, processability, etc. Furthermore, minimizing the hygroscopicity of drug substance can be one of the most challenging tasks in drug development and manufacturing.

In co-crystal development, suitable co-formers for making pharmaceutical co-crystals of a particular drug substance are typically identified by approaches based on trial and error. Thus, the selection of suitable co-formers for a drug substance and the ratio between the drug substance and the co-former to produce desirable pharmaceutical co-crystals, as well as methods for making such, are the main challenges for producing pharmaceutical co-crystals for a particular drug substance.

SUMMARY OF THE INVENTION

The present disclosure is based on, at least in part, the identification of suitable co-formers (e.g., tartaric acid and fumaric acid) for making desirable co-crystals of substituted glycine compounds (e.g., N-methylglycine) having a suitable substituted glycine compound: co-former ratio (e.g., 1:1, 2:1, 3:1, or 6:1). Such co-crystals exhibited unexpected improved properties such as hygroscopicity, processibility, and water solubility.

Accordingly, provided herein are co-crystals of a substituted glycine compound and a co-former, wherein the co-former is a compound of Formula (I) as described herein, compositions and kits comprising such, methods of making such, and uses of the co-crystals for treating and/or reducing the risk for a neuropsychiatric disorder (e.g., schizophrenia, psychotic disorders, pain or Alzheimer's disease).

In one aspect, the present disclosure provides a co-crystal of a substituted glycine compound (e.g., N-methylglycine, N-dimethylglycine, N-trimethylglycine, etc.) and a co-former, wherein the co-former is a compound of Formula (I):

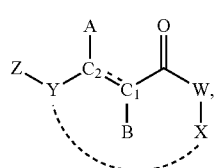

in which
A and B are independently OH or H;
W is O or NH;
X is H or absent;
Y is C=O, or $CR_1R_2$, wherein $R_1$ and $R_2$ are independently selected from H, alkyl, alkenyl, or alkynyl;
Z is OH, or —CH(OH)$R_3$, wherein the C of —CH(OH)$R_3$ is in the (R)-configuration and $R_3$ is H or alkyl; and $C_2$ ═══ $C_1$ are $C_2$-$C_1$ or $C_2$═$C_1$, wherein $C_1$ and $C_2$ are each in a $SP^3$ or $SP^2$ configuration; and Y and W can be joined by a single bond, when X is absent and either $R_1$ or $R_2$ is absent.
The molecular ratio between the substituted glycine and the co-former in the co-crystal described herein may range from 6:1 to 1:5. When $C_2$ ═══ $C_1$ are $C_2$-$C_1$, the molecular ratio between the substituted glycine and the co-former in the co-crystal may range from 1:1 to 1:5.

In certain embodiments, a co-former compound of Formula (I) is a compound of Formula (IA):

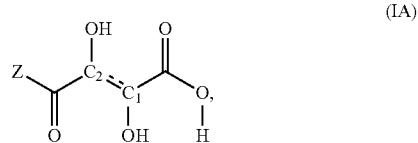

wherein $C_2$ ═══ $C_1$, and Z are as described herein. In some examples, a compound of Formula (IA) is tartaric acid

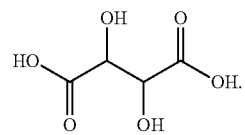

In some examples, the molecular ratio between the substituted glycine and the co-former can be 1:1.
In certain embodiments, a co-former compound of Formula (I) is a compound of Formula (IB):

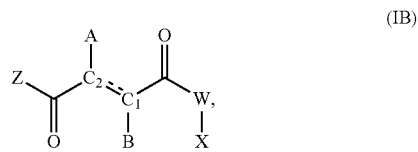

in which $C_2$ ═══ $C_1$, A, B, W, X, and Z are as defined herein. In some examples, $C_2$ ═══ $C_1$ can be $C_2$═$C_1$; A, B, or both can be hydrogen; W can be O, and/or X can be H. In one example, the compound of Formula II is fumaric acid

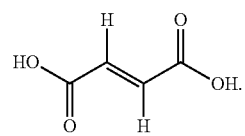

In some examples, the molecular ratio between the substituted glycine and the co-former can range from 1:2 to 6:1 (e.g., 1:1, 2:1, 3:1, or 6:1).
In certain embodiments, a co-former compound of Formula (IC) is a compound of Formula (IC):

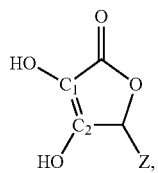

(IB)

wherein $C_1$, $C_2$, and Z are as described herein. In some embodiments, Z is —CH(OH)$R_3$, in which C is in the (R)-configuration and $R_3$ is H or alkyl (e.g., substituted by —OH such as $CH_2OH$). In one example, a compound of Formula (IC) is erythoric acid

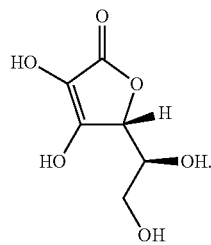 [SMILES: O=C1O[C@H]([C@@H](O)CO)C(O)=C1O]

In some examples, the molecular ratio between the substituted glycine and the co-former can be 1:1.

In any of the co-crystals described herein, the substituted glycine compound can be N-methylglycine (a.k.a., sarcosine), N-dimethylglycine, or N-trimethylglycine.

In specific examples of the co-crystals described herein:
(i) the substituted glycine is N-methylglycine, the co-former is D-tartaric acid, the molecular ratio between N-methylglycine and D-tartaric acid is 1:1 in the co-crystal, and optionally the co-crystal has a powder X-ray diffraction pattern substantially as depicted in FIG. 2 and an endothermic peak corresponding to the melting point of about 139° C.;
(ii) the substituted glycine is N-methylglycine; the co-former is L-tartaric acid, the molecular ratio between N-methylglycine and L-tartaric acid is 1:1 in the co-crystal, and optionally the co-crystal has a powder X-ray diffraction pattern substantially as depicted in FIG. 6 and an endothermic peak corresponding to the melting point of about 138° C.;
(iii) the substituted glycine is N-methylglycine, the co-former is DL-tartaric acid, the molecular ratio between N-methylglycine and DL-tartaric acid is 1:1 in the co-crystal, and optionally the co-crystal has a powder X-ray diffraction pattern substantially as depicted in FIG. 10 and an endothermic peak corresponding to the melting point of about 120° C.;
(iv) the substituted glycine is N-methylglycine, the co-former is fumaric acid, the molecular ratio between N-methylglycine and fumaric acid in the co-crystal is 1:1, and optionally the co-crystal has a powder X-ray diffraction pattern substantially as depicted in FIG. 20;
(v) the substituted glycine is N-methylglycine, the co-former is fumaric acid, the molecular ratio between N-methylglycine and fumaric acid is 2:1 in the co-crystal, and optionally the co-crystal has a powder X-ray diffraction pattern substantially as depicted in FIG. 21;
(vi) the substituted glycine is N-methylglycine, the co-former is fumaric acid, the molecular ratio between N-methylglycine and fumaric acid in the co-crystal is 3:1, and optionally the co-crystal has a powder X-ray diffraction pattern substantially as depicted in FIG. 22; or
(vii) the substituted glycine is N-methylglycine, the co-former is fumaric acid, the molecular ratio between N-methylglycine and fumaric acid in the co-crystal is 6:1, and optionally the co-crystal has a powder X-ray diffraction pattern substantially as depicted in FIG. 23.

In another aspect, the present disclosure provides compositions including an effective amount of one or more of the co-crystals described herein, and a carrier. In certain embodiments, the composition described herein is a pharmaceutical composition, which comprises a pharmaceutically acceptable carrier. In certain embodiments, the composition described herein is a nutraceutical composition. In certain embodiments, the composition described herein is a health food. In certain embodiments, the composition described herein is a medical food. Any of the compositions described herein may include an effective amount of a co-crystal as described herein. An effective amount described herein may be a therapeutically effective amount or prophylactically effective amount.

In yet another aspect, the present disclosure provides methods for treating and/or reducing the risk for a neuropsychiatric disorder (or Central Nervous System (CNS) disorders, e.g., schizophrenia, psychotic disorders, depression, suicidal ideation and/or behavior, pain, Alzheimer's disease, or dementia), the method comprising administering to a subject in need of the treatment an effective amount of any of the compositions described herein. In another aspect, the present disclosure provides methods for treating and/or reducing the risk for obesity, hypertension, a glucose or lipid metabolic disorder, e.g., the method comprising administering to a subject in need of the treatment an effective amount of any of the compositions described herein.

A target neuropsychiatric disorder can include, but is not limited to, schizophrenia, psychotic disorders, Alzheimer's disease, dementia, frontotemporal dementia, mild cognitive impairment, benign forgetfulness, closed head injury, autistic spectrum disorder (e.g., Asperger's disorder), attention deficit hyperactivity disorders, obsessive compulsive disorder, tic disorders, childhood learning disorders, premenstrual syndrome, depression, suicidal ideation and/or suicidal behavior, dysthymic disorder, bipolar disorder, anxiety disorders, post-traumatic stress disorder, chronic pain, eating disorders, addiction disorders, personality disorders, Parkinson's disorder, Huntington's disorder, or amyotrophic lateral sclerosis.

A target glucose or lipid metabolic disorder can include, but is not limited to, obesity, hypertension, diabetes, hypercholesterolemia, or hyperlipidemia.

In any of the treatment methods as described herein, the subject being treated can be a mammal (e.g., human or non-human mammal). For example, the subject can be a human patient having or suspected of having a target disease as described herein.

Another aspect of the present disclosure relates to kits comprising a container in which a co-crystal, or composition thereof, as described herein, is placed. The kits described herein may include a single dose or multiple doses of the co-crystal or composition. The kits may be useful in a method of the disclosure. In certain embodiments, the kit further includes instructions for using the co-crystal or composition.

In yet another aspect, the present disclosure provides co-crystals and compositions described herein for use in treating and/or reducing the risk for a neuropsychiatric disorder or glucose or lipid metabolic disorder as described herein and/or for manufacturing a medicament for use in treating the target diseases.

The details of one or more embodiments of the disclosure are set forth herein. Other features, objects, and advantages of the disclosure will be apparent from the Detailed Description, the Examples, and the Claims.

DEFINITIONS

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, Tables of Resolving Agents and Optical Resolutions p. 268 (E. L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-6}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, n-propyl, isopropyl, cyclopropyl, —CH$_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F, or —OH). In certain embodiments, the alkyl group is an unsubstituted $C_{1-10}$ alkyl (such as unsubstituted $C_{1-6}$ alkyl, e.g., —CH$_3$). In certain embodiments, the alkyl group is a substituted $C_{1-10}$ alkyl (such as substituted $C_{1-6}$ alkyl or substituted $C_{1-3}$ alkyl, e.g., —CF$_3$ or —CH$_2$OH).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=CHCH$_3$ or

)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

A "substituted glycine compound" refers to a compound of the Formula II:

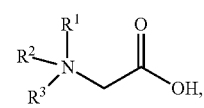

in which $R^1$, $R^2$, and $R^3$ each are independently hydrogen, alkyl, alkenyl, alkynyl, aralkyl, carbocyclyl, aryl, or heteroaryl;

In certain embodiments, the substituted glycine compound is

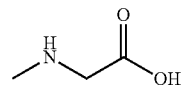

methylglycine; a.k.a., sarcosine),

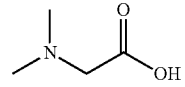

(N-dimethylglycine), or

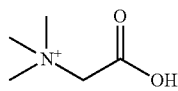

(N-trimethylglycine).

Alkyl, alkenyl, alkynyl, carbocyclyl, heterocyclyl, aryl, and heteroaryl groups, which are divalent bridging groups, are further referred to using the suffix -ene, e.g., alkylene, alkenylene, alkynylene, carbocyclylene, heterocyclylene, arylene, and heteroarylene.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups). Likewise, "saturated" refers to a group that does not contain a double or triple bond, i.e., contains all single bonds.

An atom, moiety, or group described herein may be unsubstituted or substituted, as valency permits, unless otherwise provided expressly. The term "optionally substituted" refers to substituted or unsubstituted.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N($C_{1-6}$ alkyl)C(=O)($C_{1-6}$ alkyl), —NHCO$_2$($C_{1-6}$ alkyl), —NHC(=O)N($C_{1-6}$ alkyl)$_2$, —NHC(=O)NH($C_{1-6}$ alkyl), —NHC(=O)NH$_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(NH)NH($C_{1-6}$ alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_1$ alkyl), —SO$_2$NH$_2$, —SO$_2$$C_{1-6}$ alkyl, —SO$_2$O$C_{1-6}$ alkyl, —OSO$_2$$C_{1-6}$ alkyl, —SO$C_{1-6}$ alkyl, —Si($C_{1-6}$ alkyl)$_3$, —OSi($C_{1-6}$ alkyl)$_3$-C(=S)N($C_{1-6}$ alkyl)$_2$, C(=S)NH($C_{1-4}$ alkyl), C(=S)NH$_2$, —C(=O)S($C_{1-6}$ alkyl), —C(=S)S$C_{1-6}$ alkyl, —SC(=S)S$C_{1-6}$ alkyl, —P(=O)(O$C_{1-6}$ alkyl)$_2$, —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

each instance of $R^{gg}$ is, independently, halogen, —CN, —NO$_2$, —N$_3$, —SO$_2$H, —SO$_3$H, —OH, —O$C_{1-6}$ alkyl, —ON($C_{1-6}$ alkyl)$_2$, —N($C_{1-6}$ alkyl)$_2$, —N($C_{1-6}$ alkyl)$_3$$^+$X$^-$, —NH($C_{1-6}$ alkyl)$_2$$^+$X$^-$, —NH$_2$($C_{1-6}$ alkyl)$^+$X$^-$, —NH$_3$$^+$X$^-$, —N(O$C_{1-6}$ alkyl)($C_{1-6}$ alkyl), —N(OH)($C_{1-6}$ alkyl), —NH(OH), —SH, —S$C_1$— alkyl, —SS($C_{1-6}$ alkyl), —C(=O)($C_{1-6}$ alkyl), —CO$_2$H, —CO$_2$($C_{1-6}$ alkyl), —OC(=O)($C_{1-6}$ alkyl), —OCO$_2$($C_{1-6}$ alkyl), —C(=O)NH$_2$, —C(=O)N($C_{1-6}$ alkyl)$_2$, —OC(=O)NH($C_{1-6}$ alkyl), —NHC(=O)($C_{1-6}$ alkyl), —N($C_{1-6}$ alkyl)C(=O)($C_{1-6}$ alkyl), —NHCO$_2$($C_{1-6}$ alkyl), —NHC(=O)N($C_{1-6}$ alkyl)$_2$, —NHC(=O)NH($C_{1-6}$ alkyl), —NHC(=O)NH$_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(NH)NH($C_{1-6}$ alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-4}$ alkyl), —SO$_2$NH$_2$, —SO$_2$$C_{1-6}$ alkyl, —SO$_2$O$C_{1-6}$ alkyl, —OSO$_2$$C_{1-6}$ alkyl, —SO$C_{1-6}$ alkyl, —Si($C_{1-6}$ alkyl)$_3$, —OSi($C_{1-6}$ alkyl)$_3$-C(=S)N($C_{1-6}$ alkyl)$_2$, C(=S)NH($C_{1-4}$ alkyl), C(=S)NH$_2$, —C(=O)S($C_{1-6}$ alkyl), —C(=S)S$C_{1-6}$ alkyl, —SC(=S)S$C_{1-6}$ alkyl, —P(=O)(O$C_{1-6}$ alkyl)$_2$, —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4$$^-$, PF$_4$$^-$, PF$_6$$^-$, AsF$_6$$^-$, SbF$_6$$^-$, B[3,5-(CF$_3$)$_2$C$_6$H$_3$]$_4$]$^-$, BPh$_4$$^-$, Al(OC(CF$_3$)$_3$)$_4$$^-$, and a carborane anion (e.g., CB$_{11}$H$_{12}$$^-$ or (HCB$_{11}$Me$_5$Br$_6$)$^-$). Exemplary counterions which may be multivalent include CO$_3$$^{2-}$, HPO$_4$$^{2-}$, PO$_4$$^{3-}$, B$_4$O$_7$$^{2-}$, SO$_4$$^{2-}$, S$_2$O$_3$$^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)$R^{aa}$, —CHO, —CO$_2$$R^{aa}$, —C(=O)N($R^{bb}$)$_2$, —C(=NR$^{bb}$)$R^{aa}$, —C(=NR$^{bb}$)O$R^{aa}$, —C(=NR$^{bb}$)N($R^{bb}$)$_2$, —C(=O)NR$^{bb}$SO$_2$$R^{aa}$, —C(=S)N($R^{bb}$)$_2$, —C(=O)S$R^{aa}$, or —C(=S)S$R^{aa}$, wherein $R^{aa}$ and $R^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl (e.g., aralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethylcarbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S($=$O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

Exemplary oxygen atom substituents include, but are not limited to, —R$^{aa}$, —C($=$O)SR$^{aa}$, —C($=$O)R$^{aa}$, —CO$_2$R$^{aa}$, —C($=$O)N(R$^{bb}$)$_2$, —C($=$NR$^{bb}$)R$^{aa}$, —C($=$NR$^{bb}$)OR$^{aa}$, —C($=$NR$^{bb}$)N(R$^{bb}$)$_2$, —S($=$O)R$^{aa}$, —SO$_2$R$^{aa}$, —Si(R$^{aa}$)$_3$, —P(R$^{cc}$)$_2$, —P(R$^{cc}$)$_3^+$X$^-$, —P(OR$^{cc}$)$_2$, —P(OR$^{cc}$)$_3^+$X$^-$, —P($=$O)(R$^{aa}$)$_2$, —P($=$O) (OR$^{cc}$)$_2$, and —P($=$O)(N(R$^{bb}$)$_2$)$_2$, wherein X$^-$, R$^{aa}$, R$^{bb}$, and R$^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. Exemplary oxygen protecting groups include, but are not limited to, methyl, t-butyloxycarbonyl (BOC or Boc), methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference.

Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, dimethyl sulfoxide (DMSO), tetrahydrofuran (THF), diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "crystalline" or "crystalline form" refers to a solid form substantially exhibiting three-dimensional order. In certain embodiments, a crystalline form of a solid is a solid form that is substantially not amorphous. In certain embodiments, the X-ray powder diffraction (XRPD) pattern of a crystalline form includes one or more sharply defined peaks.

The term "amorphous" or "amorphous form" refers to a form of a solid ("solid form"), the form substantially lacking three-dimensional order. In certain embodiments, an amorphous form of a solid is a solid form that is substantially not crystalline. In certain embodiments, the X-ray powder diffraction (XRPD) pattern of an amorphous form includes a wide scattering band with a peak at 2θ of, e.g., between 20 and 70°, inclusive, using CuKα radiation. In certain embodiments, the XRPD pattern of an amorphous form further includes one or more peaks attributed to crystalline structures. In certain embodiments, the maximum intensity of any one of the one or more peaks attributed to crystalline structures observed at a 2θ of between 20 and 70°, inclusive, is not more than 300-fold, not more than 100-fold, not more than 30-fold, not more than 10-fold, or not more than 3-fold of the maximum intensity of the wide scattering band. In certain embodiments, the XRPD pattern of an amorphous form includes no peaks attributed to crystalline structures.

The term "co-crystal" refers to a crystalline structure comprising at least two different components (e.g., N-methylglycine and a co-former), wherein each of the components is independently an atom, ion, or molecule. In certain embodiments, none of the components is a solvent. In certain embodiments, at least one of the components is a solvent. A co-crystal of N-methylglycine and a co-former is different from a salt formed from N-methylglycine and the co-former. In the salt, N-methylglycine is complexed with the co-former in a way that proton transfer (e.g., a complete proton transfer) from the co-former to N-methylglycine easily occurs at room temperature. In the co-crystal, however, N-methylglycine is complexed with the co-former in a way that proton transfer from the co-former to N-methylglycine does not easily occur at room temperature. In certain embodiments, in the co-crystal, there is no proton transfer from the co-former to N-methylglycine. In certain embodiments, in the co-crystal, there is partial proton transfer from the co-former to N-methylglycine. Co-crystals may be useful to improve the properties (e.g., solubility, stability, ease of formulation, or bioavailability) of N-methylglycine.

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The terms "inhibition", "inhibiting", "inhibit," or "inhibitor" refer to the ability of a co-crystal to reduce, slow, halt or prevent activity of a particular biological process in a cell relative to vehicle.

When a co-crystal, pharmaceutical composition, method, use, or kit is referred to as "selectively," "specifically," or "competitively" binding a first protein, the co-crystal binds the first protein with a higher binding affinity (e.g., not less than about 2-fold, not less than about 5-fold, not less than about 10-fold, not less than about 30-fold, not less than about 100-fold, not less than about 1,000-fold, or not less than about 10,000-fold) than binding a second protein or that is different from the first protein. When a co-crystal is referred to as "selectively," "specifically," or "competitively" modulating (e.g., increasing or inhibiting) the activity of a protein, the co-crystal modulates the activity of the protein to a greater extent (e.g., not less than about 2-fold, not less than about 5-fold, not less than about 10-fold, not less than about 30-fold, not less than about 100-fold, not less than about 1,000-fold, or not less than about 10,000-fold) than the activity of at least one protein that is different from the first protein.

The term "aberrant activity" refers to activity deviating from normal activity. The term "increased activity" refers to activity higher than normal activity.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. A "patient" refers to a human subject in need of treatment of a disease.

The terms "administer," "administering," or "administration" refers to implanting, absorbing, ingesting, injecting, inhaling, or otherwise introducing a co-crystal described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen) to delay or prevent disease occurrence. Treatment may also be continued after symptoms have resolved, for example, to delay or prevent recurrence.

The terms "condition," "disease," and "disorder" are used interchangeably.

An "effective amount" of a co-crystal described herein refers to an amount sufficient to elicit the desired biological response, i.e., treating the condition. As will be appreciated by those of ordinary skill in this art, the effective amount of a co-crystal described herein may vary depending on such factors as the desired biological endpoint, the pharmacokinetics of the co-crystal, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a co-crystal described herein in a single dose. In certain embodiments, an effective amount is the combined amounts of a co-crystal described herein in multiple doses.

A "therapeutically effective amount" of a co-crystal described herein is an amount sufficient to provide a therapeutic benefit in the treatment of a condition or to delay or minimize one or more symptoms associated with the condition. A therapeutically effective amount of a co-crystal means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a co-crystal described herein is an amount sufficient to prevent a condition, or one or more symptoms associated with the condition or prevent its recurrence. A prophylactically effective amount of a co-crystal means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "neurological disease" refers to any disease of the nervous system, including diseases that involve the central nervous system (brain, brainstem, spinal cord and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, frontotemporal dementia, Parkinson's disease, amyotrophic lateral sclerosis, tauopathies (including frontotemporal dementia), multiple system atrophy, and Huntington's disease.

Examples of neurological diseases include, but are not limited to, headache, stupor and coma, dementia, seizure, sleep disorders, trauma, infections, neoplasms, neuro-ophthalmopathy, movement disorders, demyelinating diseases, spinal cord disorders, and disorders of peripheral nerves, muscle and neuromuscular junctions. Addiction and mental illness, include, but are not limited to, depression, suicidal ideation and/or behavior, bipolar disorder and schizophrenia, are also included in the definition of neurological diseases or CNS disorders. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; chronic pain; Batten disease; Behcet's disease; Bell's palsy; benign essential blepharospasm; benign focal amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal cord tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

The term "psychiatric disorder" refers to mental disorders and includes diseases and disorders listed in the Diagnostic and Statistical Manual of Mental Disorders—Fourth Edition and Fifth Edition (DSM-IV, DSM-V), published by the American Psychiatric Association, Washington D.C. (1994, 2015). Psychiatric disorders include, but are not limited to, anxiety disorders (e.g., acute stress disorder, agoraphobia, generalized anxiety disorder, obsessive-compulsive disorder, panic disorder, posttraumatic stress disorder, separation anxiety disorder, social phobia, and specific phobia), childhood disorders, (e.g., attention-deficit/hyperactivity disorder, conduct disorder, and oppositional defiant disorder), eating disorders (e.g., anorexia nervosa and bulimia nervosa), mood disorders (e.g., depression, bipolar disorder I and II, cyclothymic disorder, dysthymic disorder, and major depressive disorder), suicidal ideation and/or behavior, personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders (e.g., alcohol dependence or abuse, amphetamine dependence or abuse, cannabis dependence or abuse, cocaine dependence or abuse, hallucinogen dependence or abuse, inhalant dependence or abuse, nicotine dependence or abuse, opioid dependence or abuse, phencyclidine dependence or abuse, and sedative dependence or abuse), adjustment disorders, autism, Asperger's disorder, autistic disorder, delirium, dementia, multi-infarct dementia, learning and memory disorders (e.g., amnesia and age-related memory loss), and Tourette's disorder.

The term "neuropsychiatric disorder," including either neurological diseases or psychiatric disorders or CNS disorders, or refers to a disorder that involves either psychiatric symptoms or syndromes caused by organic brain disorders. The main characteristics of neuropsychiatric symptoms include occurrence of the various psychiatric symptoms, cognitive impairment, neurological symptoms or the possibility of early cerebral development symptoms.

The terms "health food" or "health food product" refers to any kind of liquid and solid/semi-solid materials that are used for nourishing humans and animals, for improving basic behavioral functioning, hyperactivity, anxiety, depression, sensorimotor gating, pain threshold, memory and/or cognitive functioning, body weight, or for facilitating treatment of any of the target diseases noted herein. The term "nutraceutical composition" refers to compositions containing components from food sources and conferring extra health benefits in addition to the basic nutritional value found in foods.

The term "medical food product" refers to a food product formulated to be consumed or administered enterally, including a food product that is usually used under the supervision of a physician for the specific dietary management of a target disease, such as those described herein. A "medical food product" composition may refer to a composition that is specially formulated and processed (as opposed to a naturally occurring foodstuff used in a natural state) for a patient in need of the treatment (e.g., human patients who suffer from illness or who requires use of the product as a major active agent for alleviating a disease or condition via specific dietary management).

DETAILED DESCRIPTION

Figure 1:
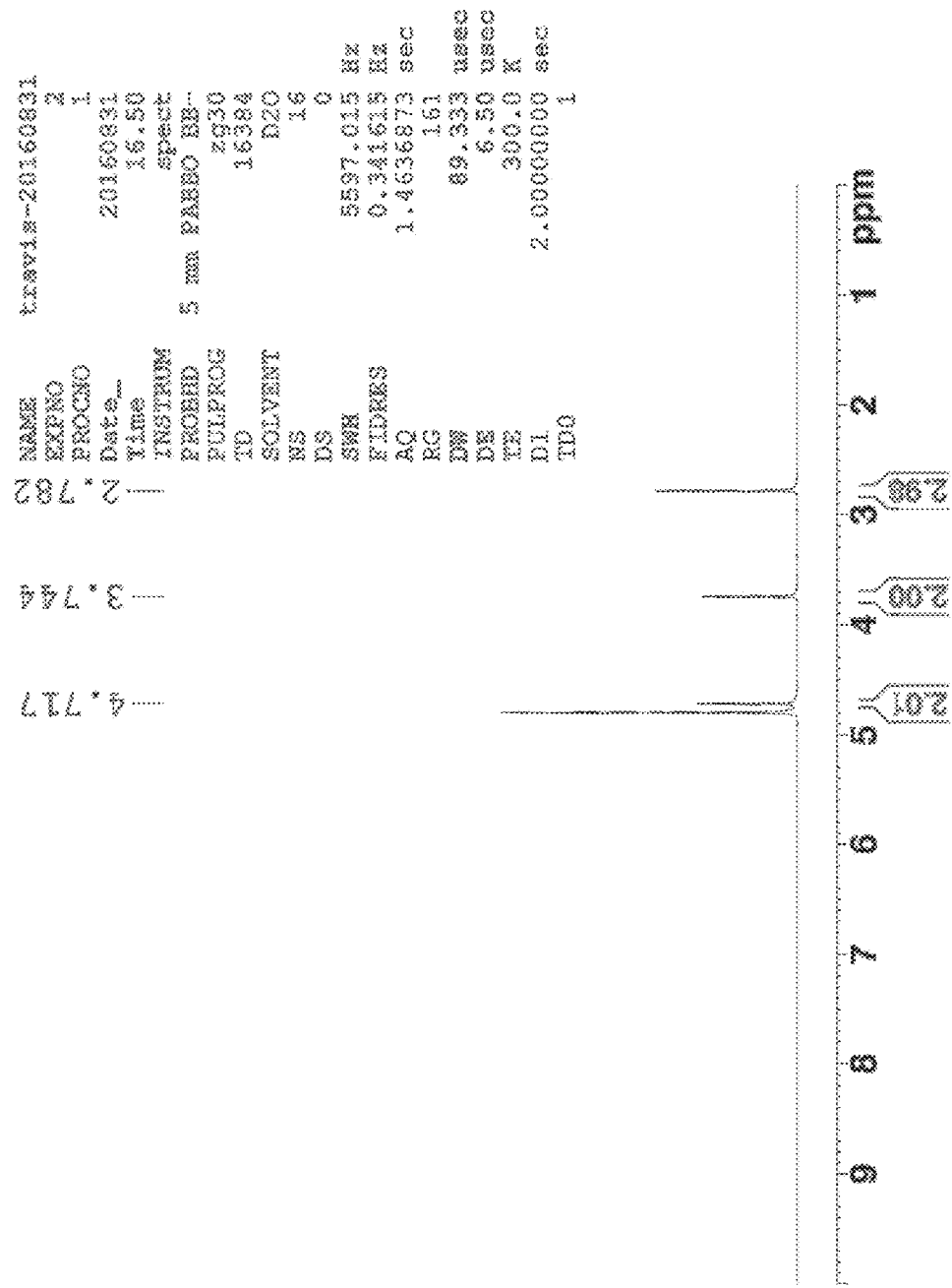
FIG. 1 shows the $^1$H-NMR analysis of N-methylglycine: D-tartaric acid (1:1 co-crystal) from Example 1.

The present disclosure provides co-crystals of a substituted glycine compound such as N-methylglycine, N-dimethylglycine, or N-trimethylglycine, and a co-former, which is a compound of Formula (I) as described herein. Such co-crystals are expected to possess advantageous physical, chemical, physiologic, and/or therapeutic features as relative to the substituted glycine compound in non-co-crystal form or in different co-crystal form. For example, the substituted glycine co-crystals are expected to show advantageous properties, including improved hygroscopicity, solubility, dissolution rate, physical stability, chemical stability, bioavailability, processability, and superior pharmacokinetic or therapeutic properties. The co-crystals are useful in treating and/or reducing the risk for various diseases and disorders, including neuropsychiatric disorders in a subject. Thus, also provided herein are methods of preparing the co-crystals, compositions, kits, and methods of using the co-crystals described herein for treating and/or reducing the risk for any of the target diseases described herein.

Co-Crystals of Substituted Glycine Compound and Co-Former

One aspect of the present disclosure relates to the co-crystals of a substituted glycine compound and a co-former as described herein, as well as their hydrates, polymorphs, tautomers, stereoisomers, isotopically labeled derivatives, or prodrugs. These co-crystals are useful in treating and/or reducing the risk for neuropsychiatric disorders in a subject.

In certain embodiments, a co-crystal described herein is a co-crystal of a substituted glycine compound such as N-methylglycine, N-dimethylglycine, or N-trimethylglycine and a co-former, wherein the co-former is a compound of Formula (I):

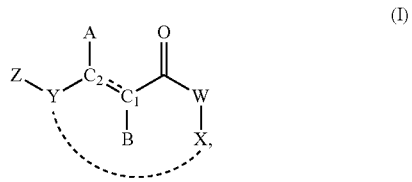

(I)

in which A, B, W, X, Y, Z, and $C_2\text{-----}C_1$ are as described herein, or a solvate, hydrate, polymorph, tautomer, stereoisomer, isotopically labeled derivative, or prodrug thereof.

In Formula (I), in some embodiments, A can be OH. In some embodiments, A can be H.

In Formula (I), in some embodiments, B can be OH. In some embodiments, B can be H.

In Formula (I), in some embodiments, W can be O. In some embodiments, W can be NH.

In Formula (I), in some embodiments, X can be H. In some embodiments, X can be absent.

In some embodiments, Y can be C=O. In some embodiments, Y can be —$CR_1R_2$, wherein $R_1$ and $R_2$ are independently H, alkyl, alkenyl, or alkynyl. In some embodiments, Y can be —$CH_2$. In some embodiments, Y can be —CH ($C_{1-6}$ alkyl) (e.g., —CHMe, or —CHEt). In some embodiments, Y can be —C($C_{1-6}$ alkyl)$_2$ (e.g., —CMe$_2$, or —CEt$_2$).

In some embodiments, Z can be OH. In some embodiments, Z can be —CH(OH)$R_3$, wherein the C of —CH(OH)$R_3$ is in the (R)-configuration and $R_3$ can be H or alkyl (which may be substituted, for example, with an —OH group). In some embodiments, Z can be a $C_{1-3}$ alkyl substituted with —OH (e.g., CH$_2$OH). In some embodiments, Z can be —C(OH)H$_2$. In some embodiments, Z can be —CH(OH)Me. In some embodiments, Z can be —CH(OH)Et.

In some embodiments, $C_2\text{-----}C_1$ is $C_2$-AC wherein $C_2$ and $C_1$ are connected via a single bond. In some embodiments, $C_2\text{-----}C_1$ is $C_2$=$C_1$, wherein $C_1$ and $C_2$ are connected via a double bond. In some embodiments, for $C_2\text{-----}C_1$, $C_1$ and $C_2$ are each carbon in a SP$^3$ or SP$^2$ configuration.

In some embodiments, the substituted glycine compound and the co-former of Formula (I) can exist in the co-crystal in a molecular ratio ranging from 1:0.5 to 1:1.5, but excluding 1:0.5. In some embodiments, the substituted glycine compound and the co-former of Formula (I) can exist in the co-crystal in a molecular ratio ranging from 1:0.6 to 1:1.4. In some embodiments, the substituted glycine compound and the co-former of Formula (I) can exist in the co-crystal in a molecular ratio ranging from 1:0.7 to 1:1.3. In some embodiments, the substituted glycine compound and the co-former of Formula (I) can exist in the co-crystal in a molecular ratio ranging from 1:1 to 1:1.5, for example, 1:1 to 1:1.3. In some embodiments, the substituted glycine compound and the co-former of Formula (I) can exist in the co-crystal in a molecular ratio ranging from 1:1 to 1:1.2. In some embodiments, the substituted glycine compound and the co-former of Formula (I) can exist in the co-crystal in a molecular ratio ranging from 1:1 to 1:1.1. In some embodiments, the substituted glycine compound and the co-former of Formula (I) can exist in the co-crystal in a molecular ratio of 1:1.

In some embodiments, a co-former compound of Formula (I) is of the Formula (IA):

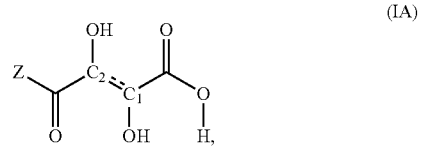

(IA)

wherein $C_2\text{-----}C_1$ and Z are described herein. In some embodiments, the co-former compound is of the formula:

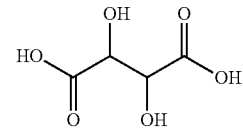

(tartaric acid). In some embodiments, the co-former compound is L-tartaric acid. In some embodiments, the co-former compound is D-tartaric acid. In some embodiments, the co-former compound is DL-tartaric acid. In some embodiments, the co-former compound is meso-tartaric acid.

In some embodiments, the substituted glycine compound and the co-former of Formula (IA) can exist in the co-crystal in a molecular ratio ranging from 1:0.5 to 1:1.5, but excluding 1:0.5. In some embodiments, the substituted glycine compound and the co-former of Formula (IA) can exist in the co-crystal in a molecular ratio ranging from 1:0.6 to 1:1.4. In some embodiments, the substituted glycine compound and the co-former of Formula (IA) can exist in the co-crystal in a molecular ratio ranging from 1:0.7 to 1:1.3. In some embodiments, the substituted glycine compound and the co-former of Formula (IA) can exist in the co-crystal in a molecular ratio ranging from 1:1 to 1:1.5, for example, 1:1 to 1:1.3. In some embodiments, the substituted glycine compound and the co-former of Formula (IA) can exist in the co-crystal in a molecular ratio ranging from 1:1 to 1:1.2. In some embodiments, the substituted glycine compound and the co-former of Formula (IA) can exist in the co-crystal in a molecular ratio ranging from 1:1 to 1:1.1. In some embodiments, the substituted glycine compound and the co-former of Formula (IA) can exist in the co-crystal in a molecular ratio of 1:1.

In certain embodiments, a co-crystal described herein is a co-crystal of a substituted glycine compound such as N-methylglycine and a co-former, wherein the co-former is a compound of Formula (IB):

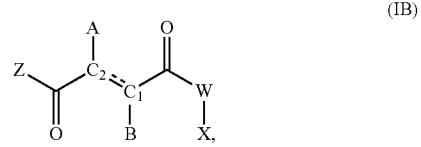

(IB)

in which $C_2\text{-----}C_1$, A, B, W, X, and Z are described herein, or a solvate, hydrate, polymorph, tautomer, stereoisomer, isotopically labeled derivative, or prodrug thereof.

In Formula (IB), in some embodiments, A can be H and B can be H. In some embodiments, A can be OH and B can be H. In some embodiments, A can be H and B can be OH.

In Formula (IB), in some embodiments, W can be O. In some embodiments, W can be NH.

In Formula (IB), in some embodiments, X can be H

In Formula (IB), in some embodiments, Z can be OH. In some embodiments, Z can be $NH_2$.

In some embodiments, $C_2 \text{=\!=\!=\!=} C_1$ is $C_2\text{-}C_1$ wherein $C_2$ and $C_1$ are connected via a single bond. In some embodiments, $C_2 \text{=\!=\!=\!=} C_1$ is $C_2\text{=}C_1$, wherein $C_1$ and $C_2$ are connected via a double bond. In some embodiments, for $C_2 \text{=\!=\!=\!=} C_1$, $C_1$ and $C_2$ are each carbon in a $SP^3$ or $SP^2$ configuration.

In some embodiments, the co-former of Formula (IB) is

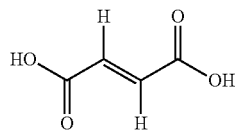

(fumaric acid), and the substituted glycine compound and this co-former can exist in the co-crystal in the molecular ratio ranging from 1:2 to 6:1. In some embodiments, the substituted glycine compound and the co-former can exist in the co-crystal in the molecular ratio ranging from 1:1 to 5:1. In some embodiments, the substituted glycine compound and the co-former can exist in the co-crystal in the molecular ratio ranging from 2:1 to 4:1. In some embodiments, the substituted glycine compound and the co-former can exist in the co-crystal in the molecular ratio ranging from 2:1 to 3:1. In some embodiments, the substituted glycine compound and the co-former can exist in the co-crystal in the molecular ratio of 2:1. In some embodiments, the substituted glycine compound and the co-former can exist in the co-crystal in the molecular ratio of 1:1. In some embodiments, the substituted glycine compound and the co-former can exist in the co-crystal in the molecular ratio of 1:1.5. In some embodiments, the substituted glycine compound and the co-former can exist in the co-crystal in the molecular ratio of 1:2.

Figure 2:
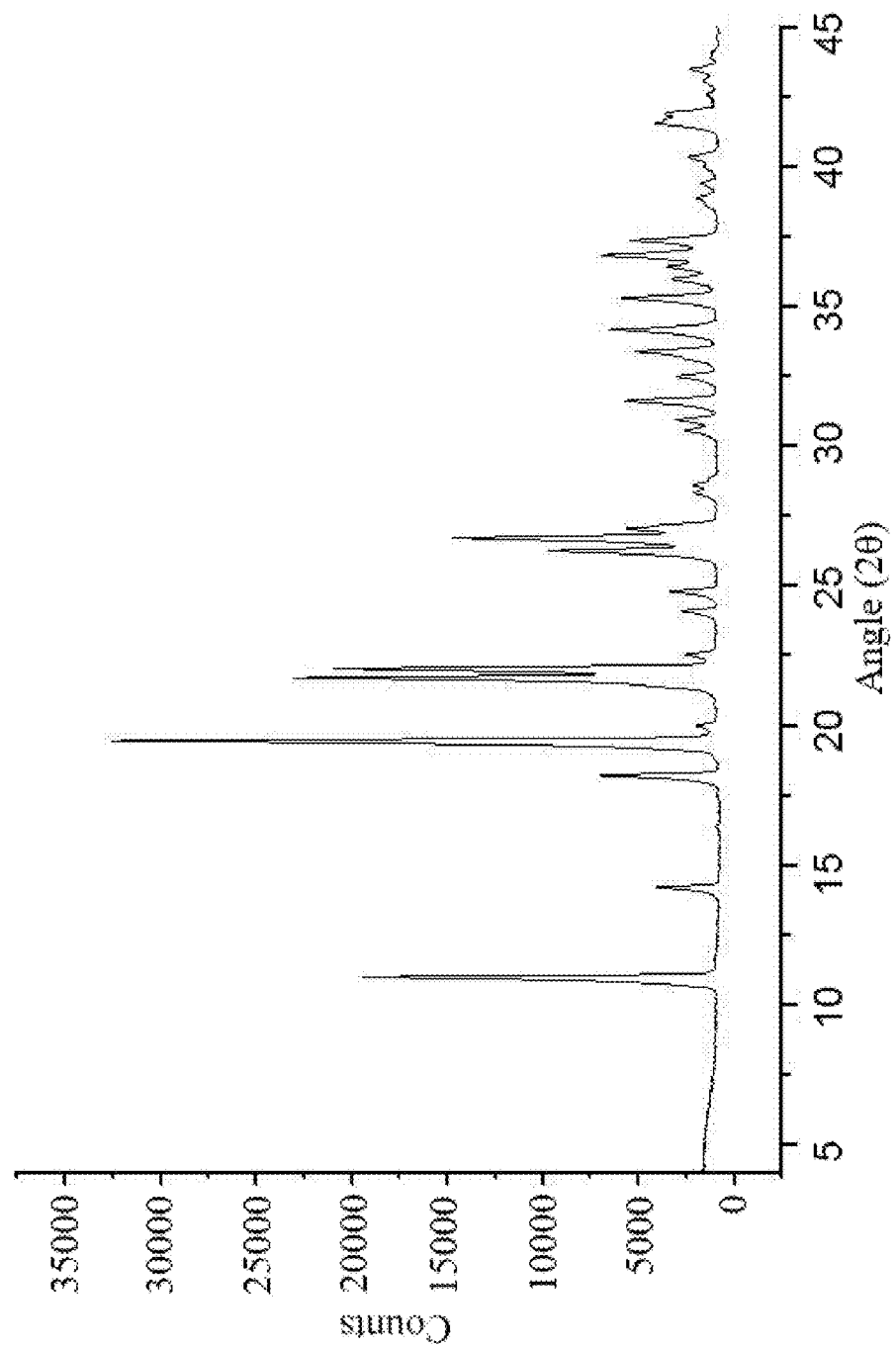
FIG. 2 shows the X-ray powder diffraction (XRPD) of N-methylglycine: D-tartaric acid (1:1 co-crystal) from Example 1, at a 2θ angle with peaks (°) of: 11.0, 14.2, 18.2, 19.4, 19.9, 21.6, 22.0, 22.5, 24.0, 24.8, 26.2, 26.7, 27.0, 28.3, 28.6, 30.5, 30.9, 31.6, 32.4, 33.3, 34.1, 35.3, 35.9, 36.4, 36.8, 37.3, 38.6, 38.9, 39.4, 40.0, 40.3, 41.5, 41.8, 41.9, 42.1, 42.2, 42.3, 42.5, 42.6, 42.8, 43.0, 43.3, 43.5, 43.8, 44.0, and 44.1.
Figure 3:
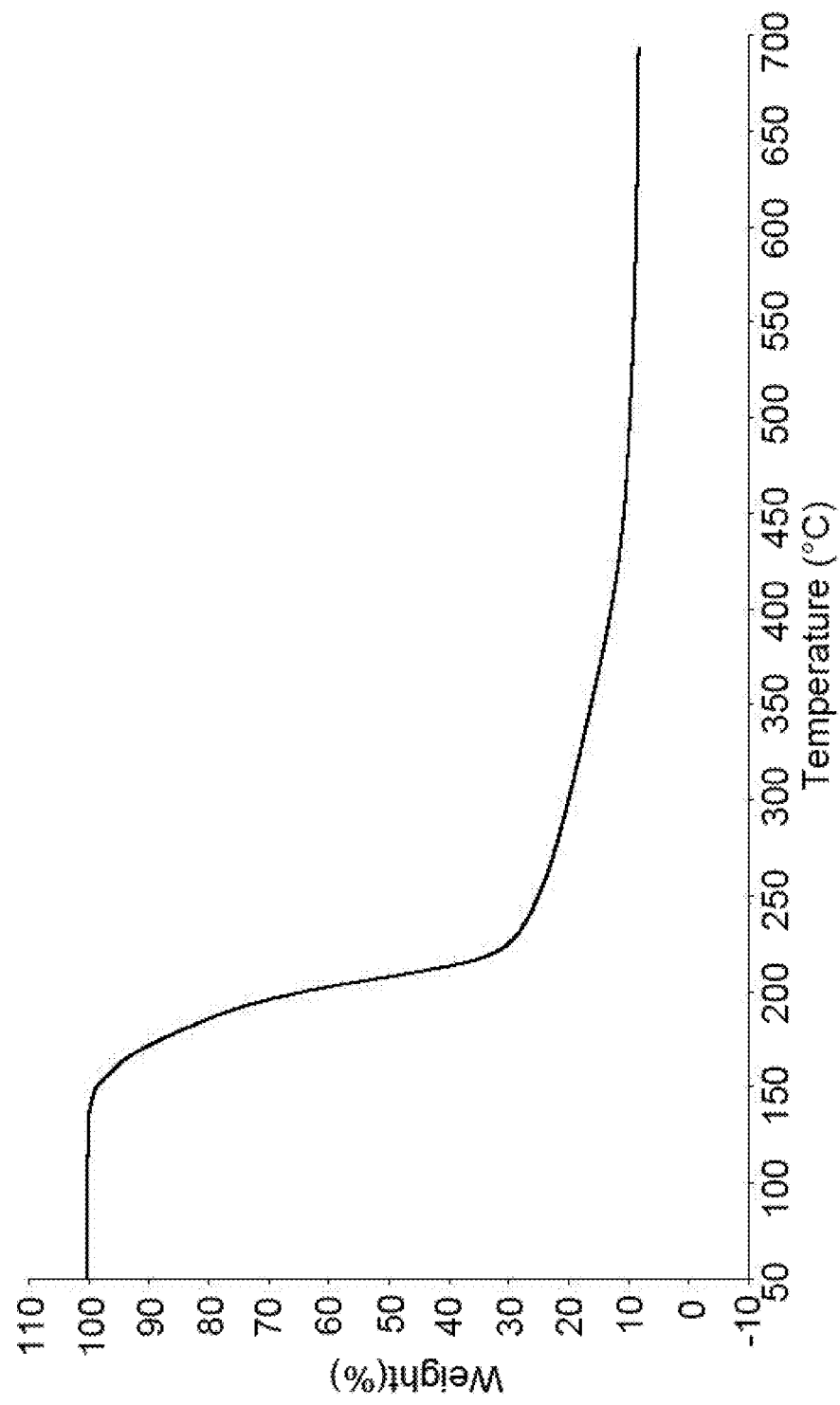
FIG. 3 shows the Thermogravimetric Analysis (TGA) of N-methylglycine:D-tartaric acid (1:1 co-crystal) from Example 1.
Figure 4:
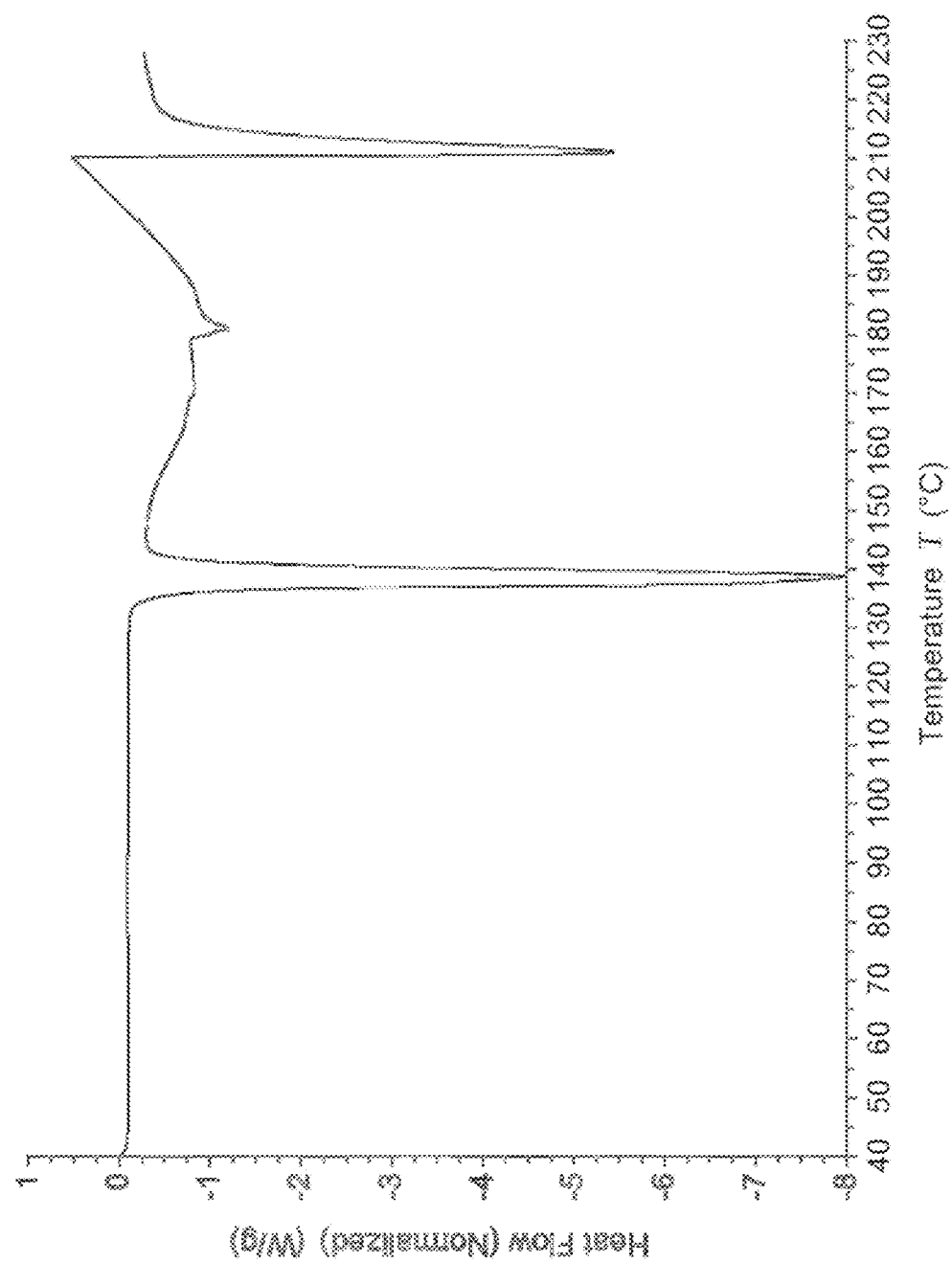
FIG. 4 shows the Differential Scanning Calorimeter (DSC) data of N-methylglycine:D-tartaric acid (1:1 co-crystal) from Example 1.
Figure 5:
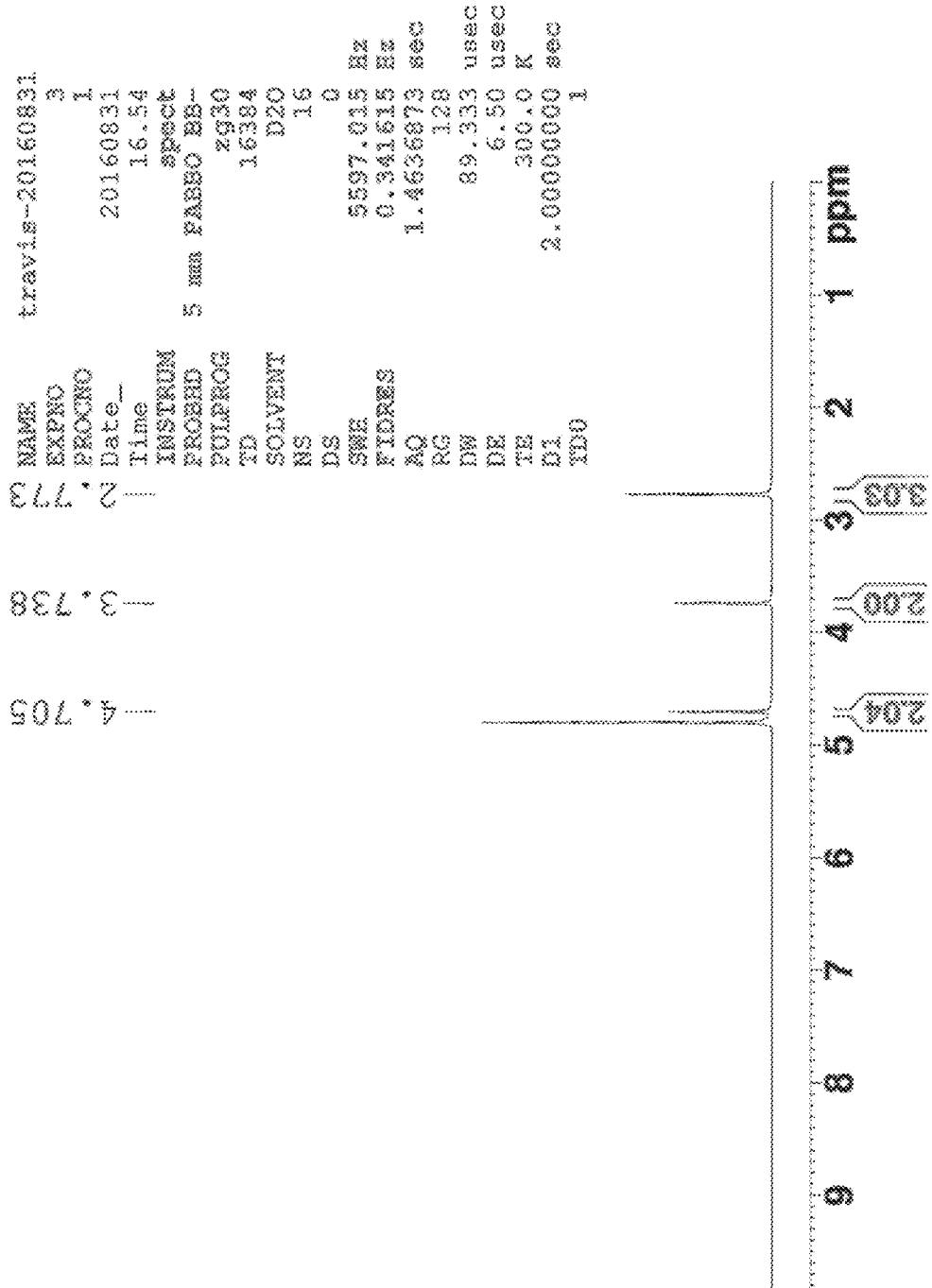
FIG. 5 shows the $^1$H-NMR of N-methylglycine:L-tartaric acid (1:1 co-crystal) from Example 2.
Figure 6:
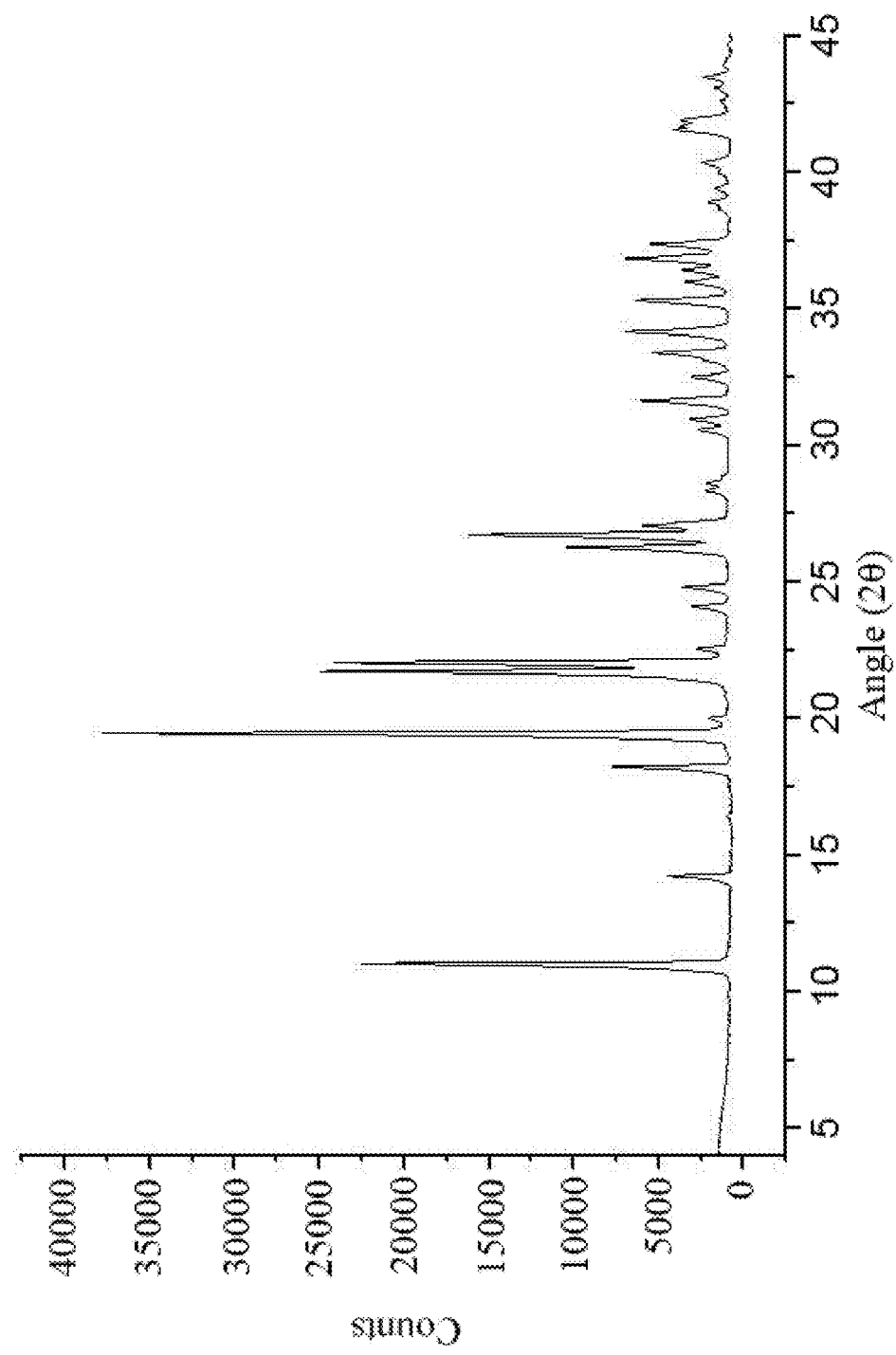
FIG. 6 shows the X-ray powder diffraction (XRPD) of N-methylglycine:L-tartaric acid (1:1 co-crystal) from Example 2, at a 2θ angle with peaks (°) of: 11.0, 14.2, 18.2, 19.4, 20.0, 21.7, 22.0, 22.5, 24.1, 24.8, 26.2, 26.7, 27.0, 28.3, 28.6, 28.8, 30.5, 30.9, 31.6, 32.5, 33.1, 33.3, 34.1, 35.3, 35.9, 36.4, 36.8, 37.3, 38.6, 38.8, 39.3, 40.0, 40.3, 41.5, 41.6, 41.9, 42.5, 43.0, 43.4, and 43.9.
Figure 7:
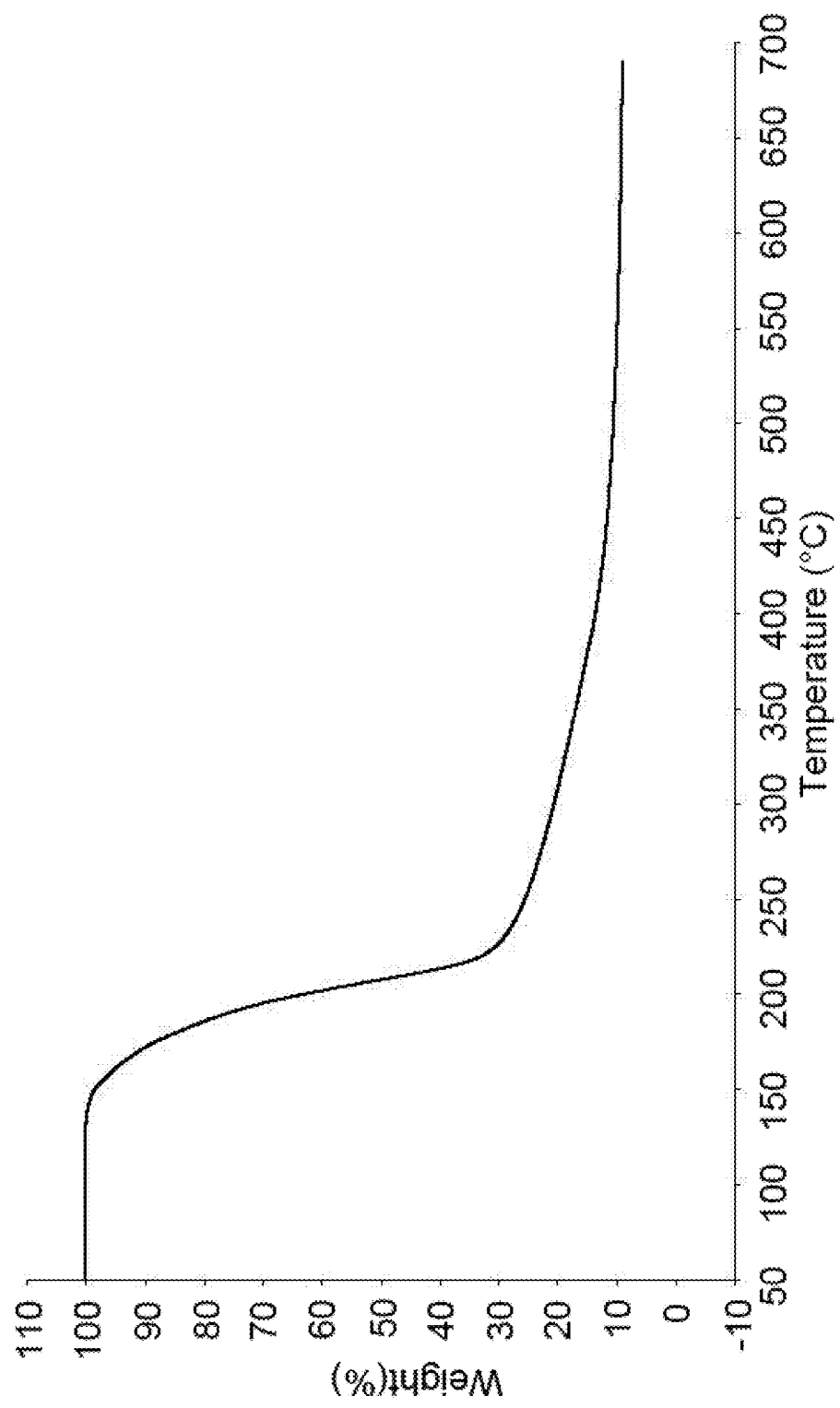
FIG. 7 shows the TGA of N-methylglycine:L-tartaric acid (1:1 co-crystal) from Example 2.
Figure 8:
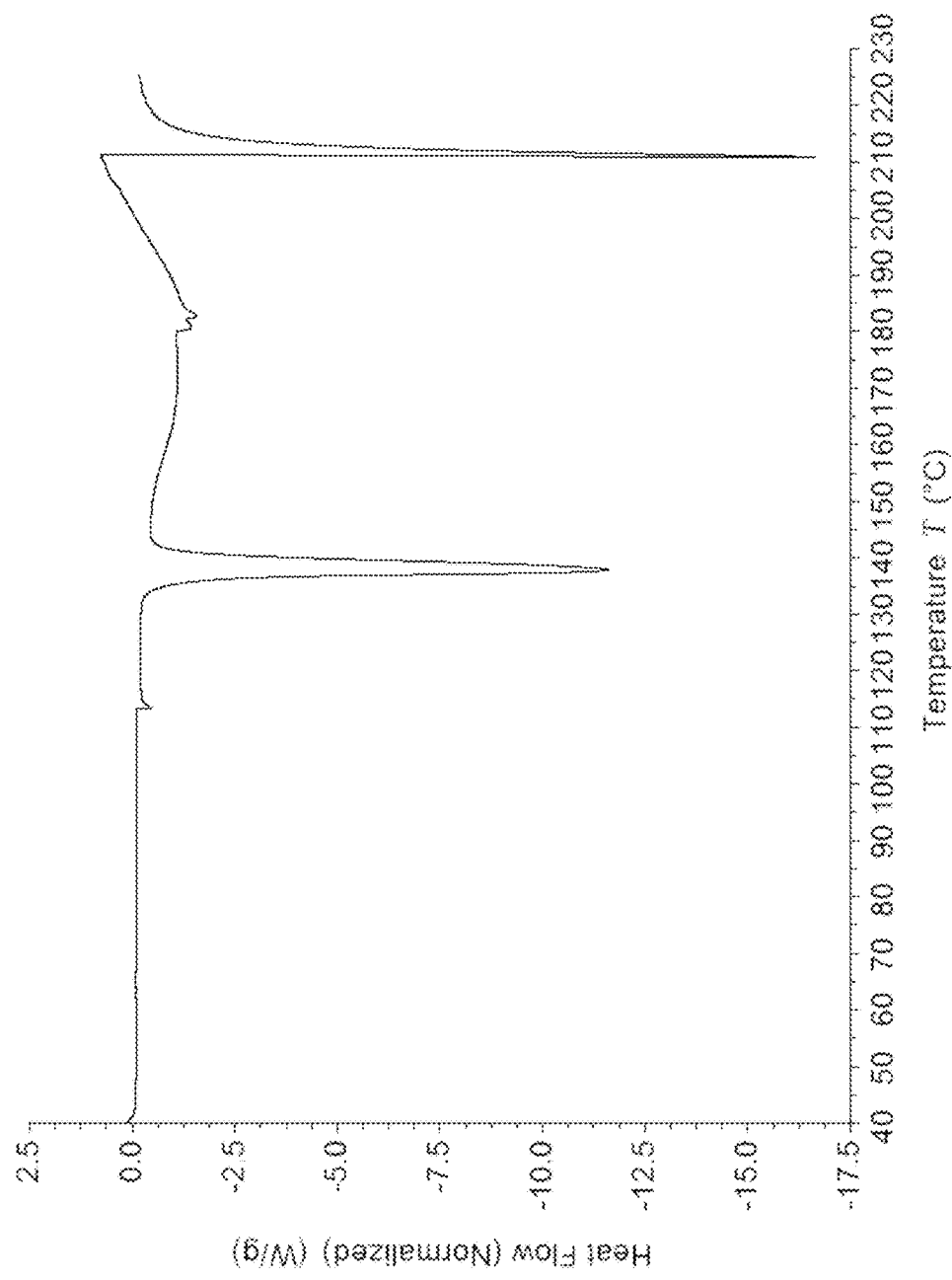
FIG. 8 shows the DSC of N-methylglycine:L-tartaric acid (1:1 co-crystal) from Example 2.
Figure 9:
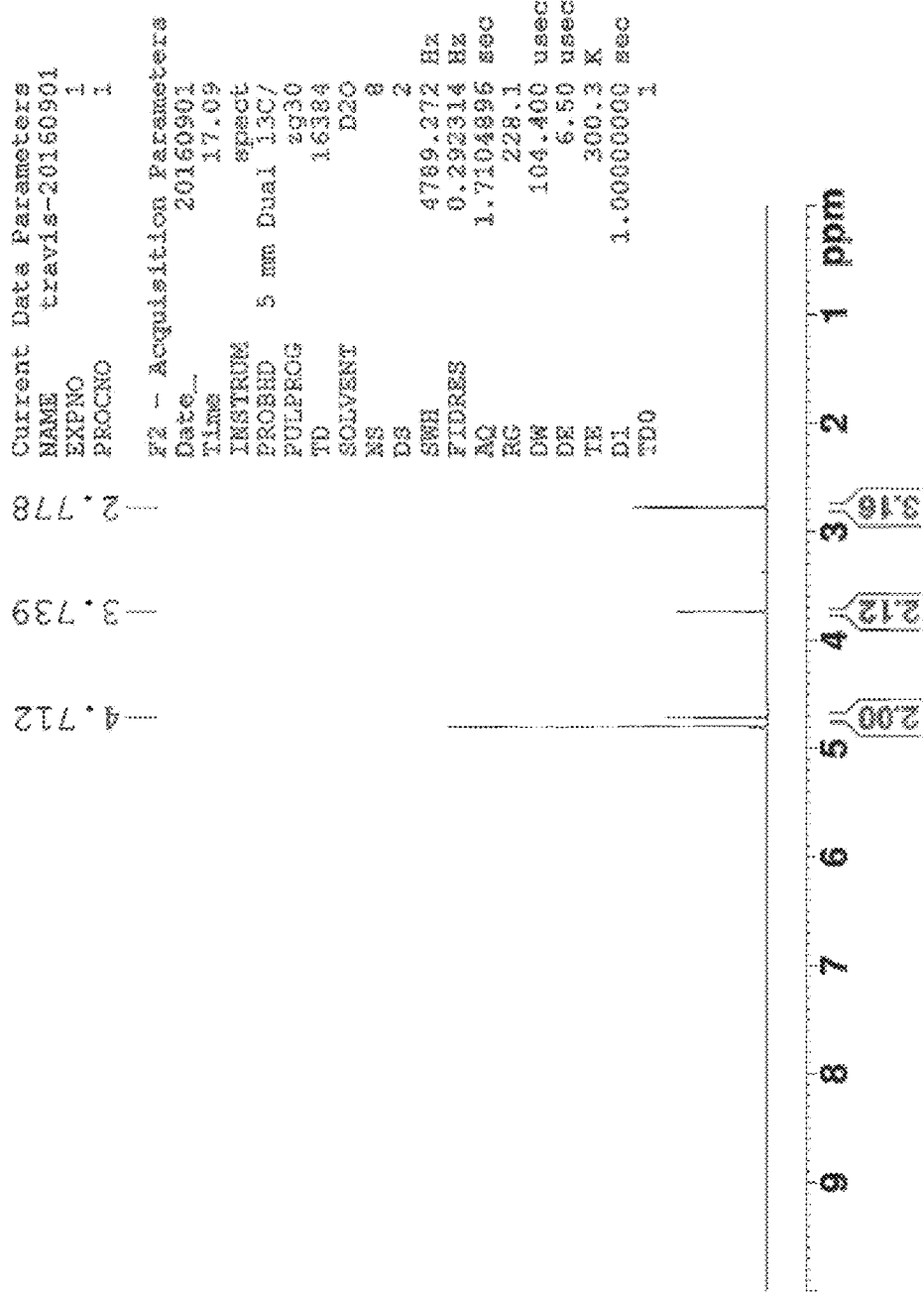
FIG. 9 shows the $^1$H-NMR of N-methylglycine:DL-tartaric acid (1:1 co-crystal) from Example 3.
Figure 10:
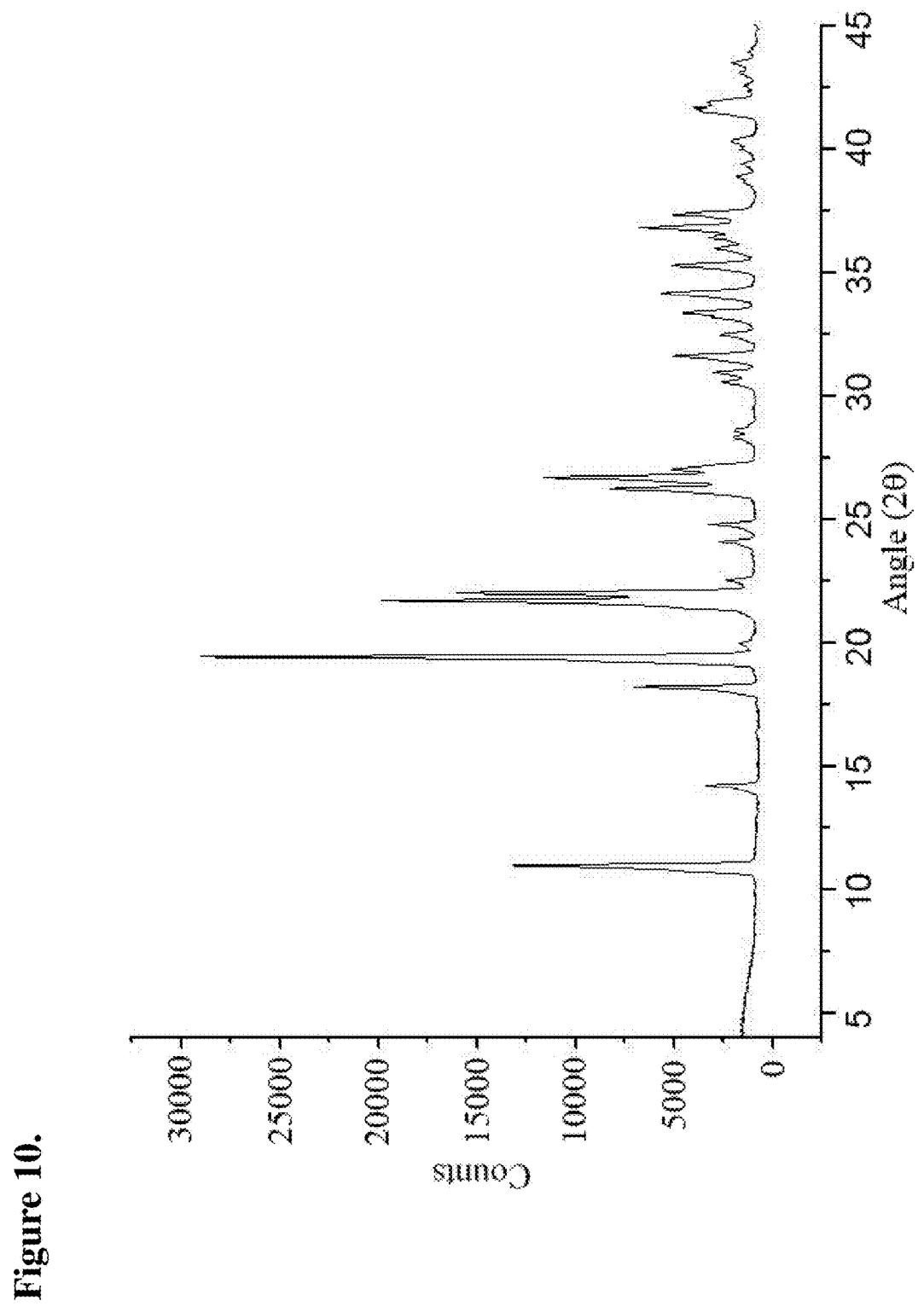
FIG. 10 shows the XRPD of N-methylglycine:DL-tartaric acid (1:1 co-crystal) from Example 3, at a 2θ angle with peaks (°) of: 10.9, 14.2, 18.2, 19.4, 19.9, 21.7, 22.0, 22.5, 24.0, 24.8, 26.2, 26.6, 27.0, 28.3, 28.5, 28.8, 30.5, 30.9, 31.5, 32.4, 33.1, 33.3, 34.1, 35.2, 35.9, 36.4, 36.8, 37.3, 38.6, 38.8, 39.3, 39.9, 40.0, 40.2, 41.5, 41.6, 41.8, 42.3, 42.5, 42.9, 43.0, 43.4, and 43.8.
Figure 11:
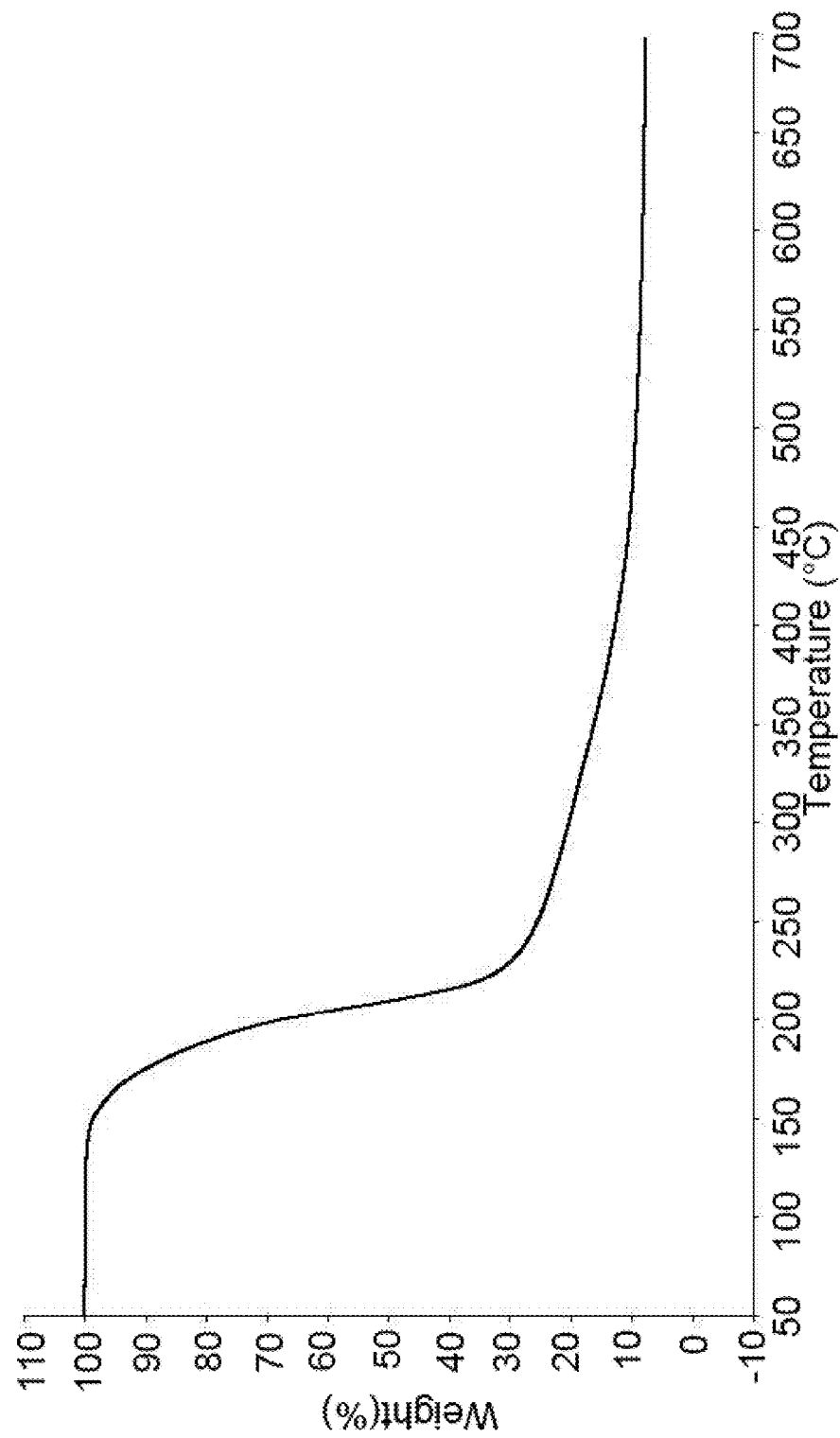
FIG. 11 shows the TGA of N-methylglycine:DL-tartaric acid (1:1 co-crystal) from Example 3.
Figure 12:
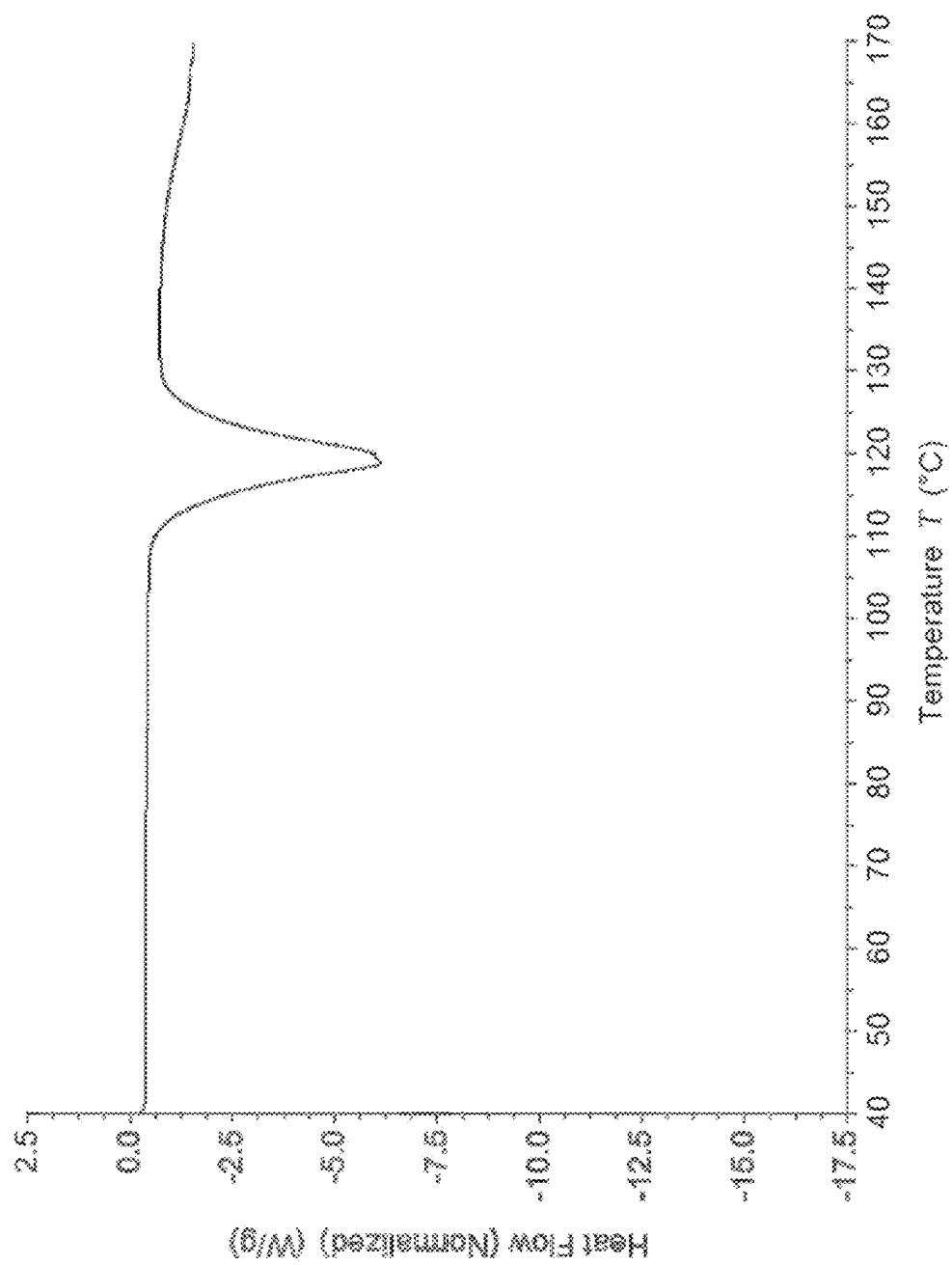
FIG. 12 shows the DSC of N-methylglycine:DL-tartaric acid (1:1 co-crystal) from Example 3.
Figure 13:
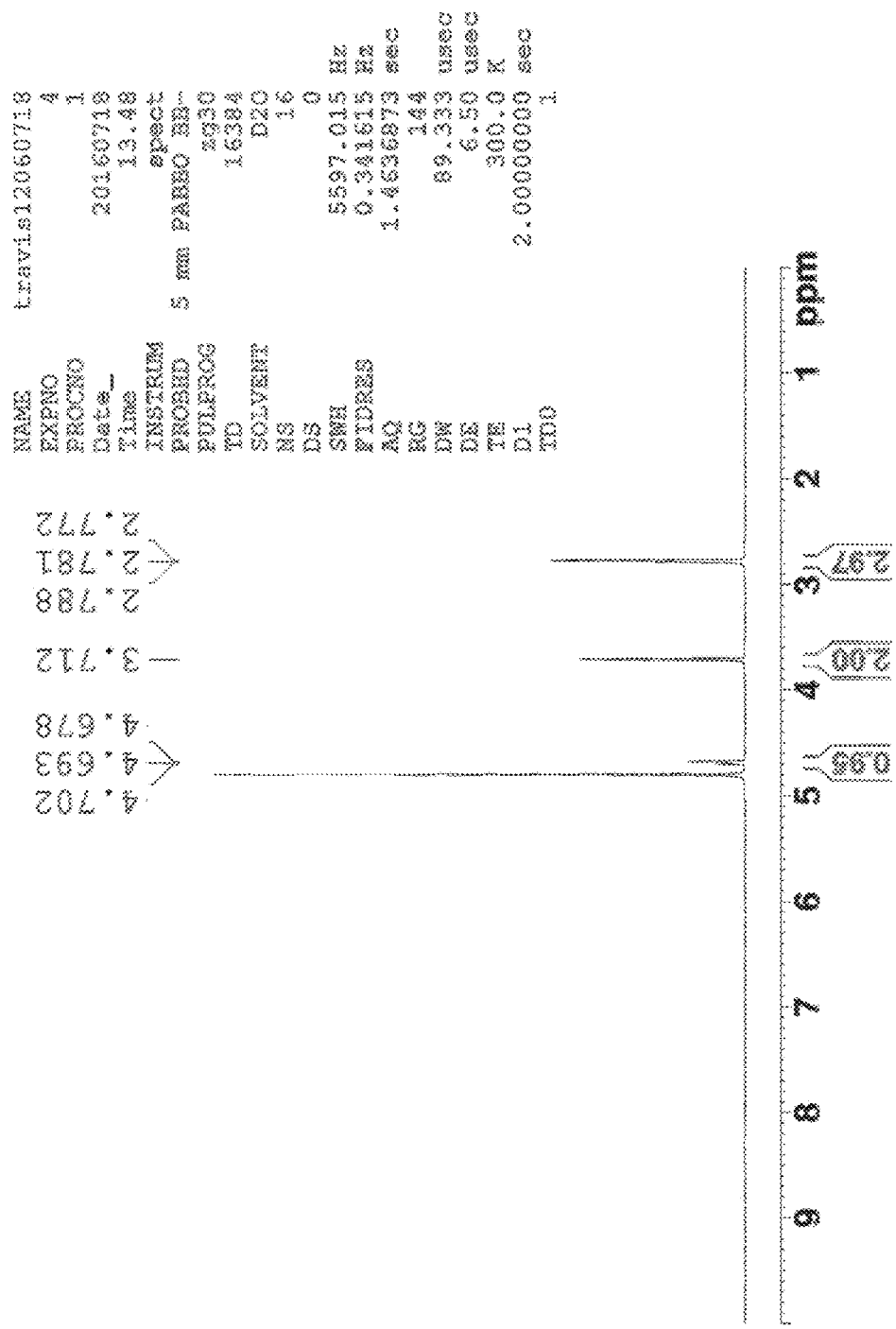
FIG. 13 shows the $^1$H-NMR of N-methylglycine:L-tartaric acid (2:1 co-crystal) from Example 4.
Figure 14:
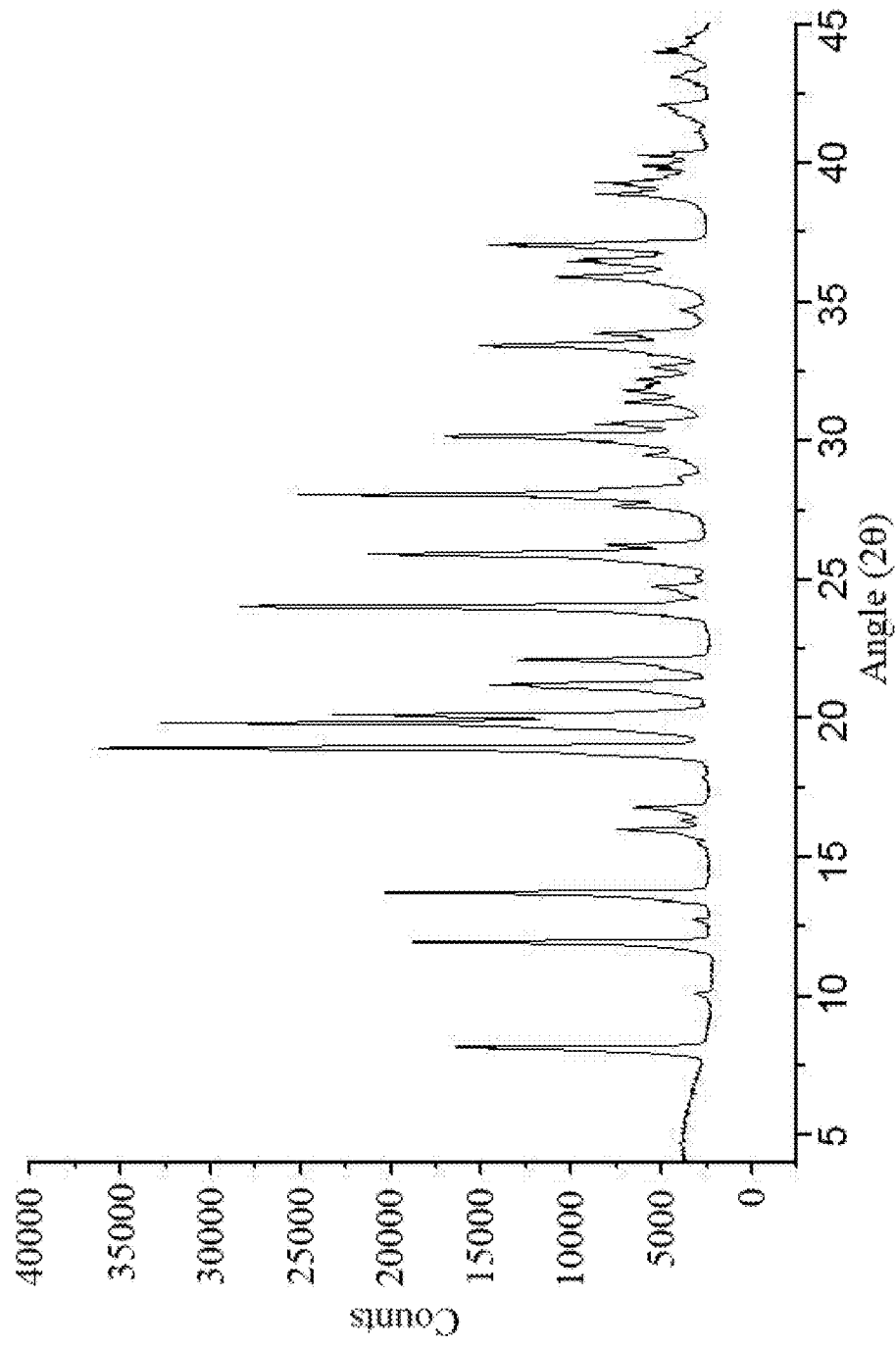
FIG. 14 shows the XRPD of N-methylglycine:L-tartaric acid (2:1 co-crystal) from Example 4, at a 2θ angle with peaks (°) of: 8.1, 10.0, 11.9, 12.7, 13.3, 13.7, 15.5, 15.9, 16.3, 16.7, 17.8, 18.9, 19.8, 20.1, 21.2, 22.1, 24.0, 24.7, 25.0, 25.9, 26.2, 27.6, 28.0, 28.6, 29.4, 29.9, 30.1, 30.2, 30.6, 31.3, 31.8, 31.9, 32.2, 32.6, 33.4, 33.8, 34.7, 35.8, 36.4, 37.0, 38.8, 39.2, 39.7, 39.9, 40.2, 41.1, 41.5, 41.8, 41.9, 42.0, 42.8, 42.9, 43.1, 44.0, 44.1, and 44.5.
Figure 15:
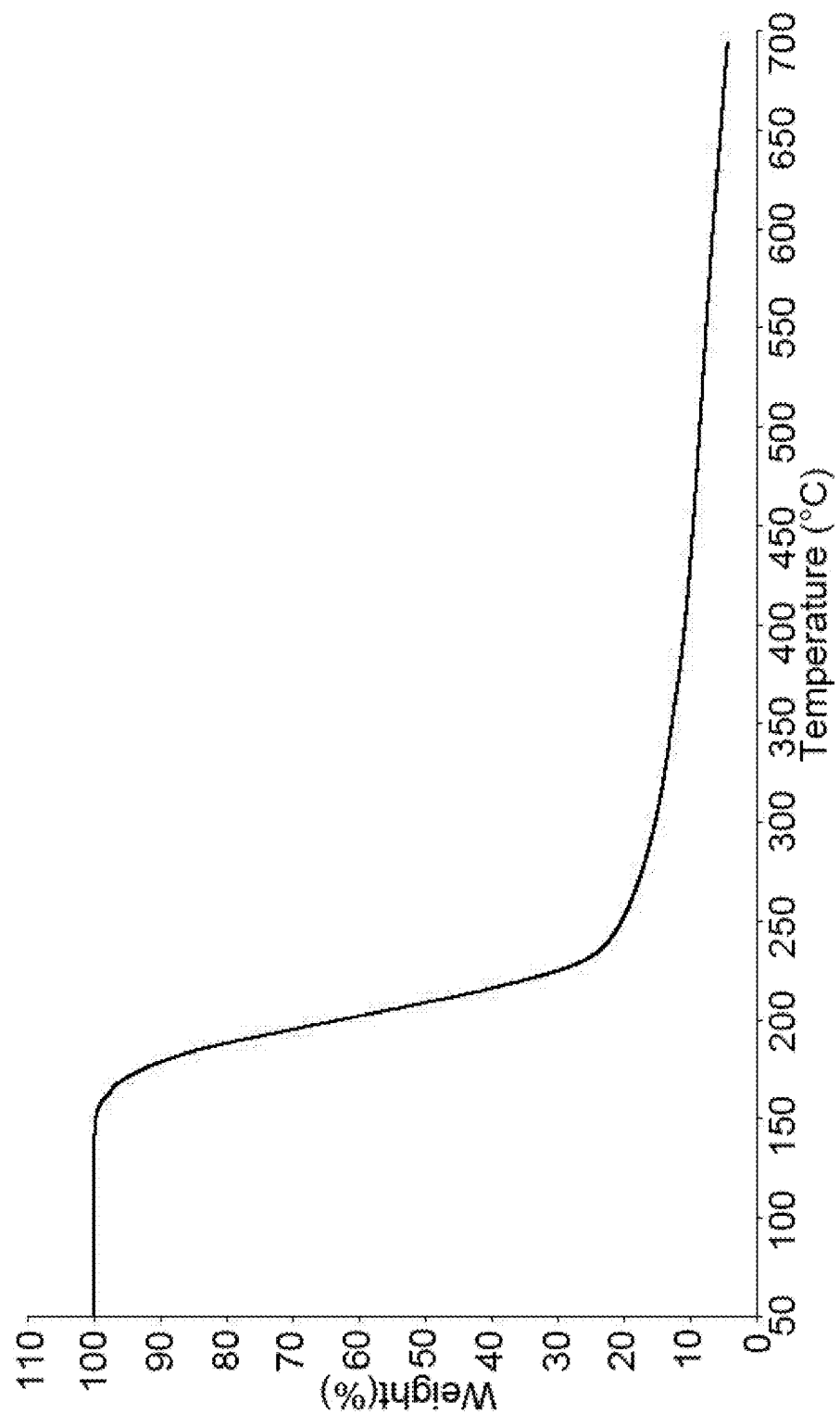
FIG. 15 shows the TGA of N-methylglycine:L-tartaric acid (2:1 co-crystal) from Example 4.
Figure 16:
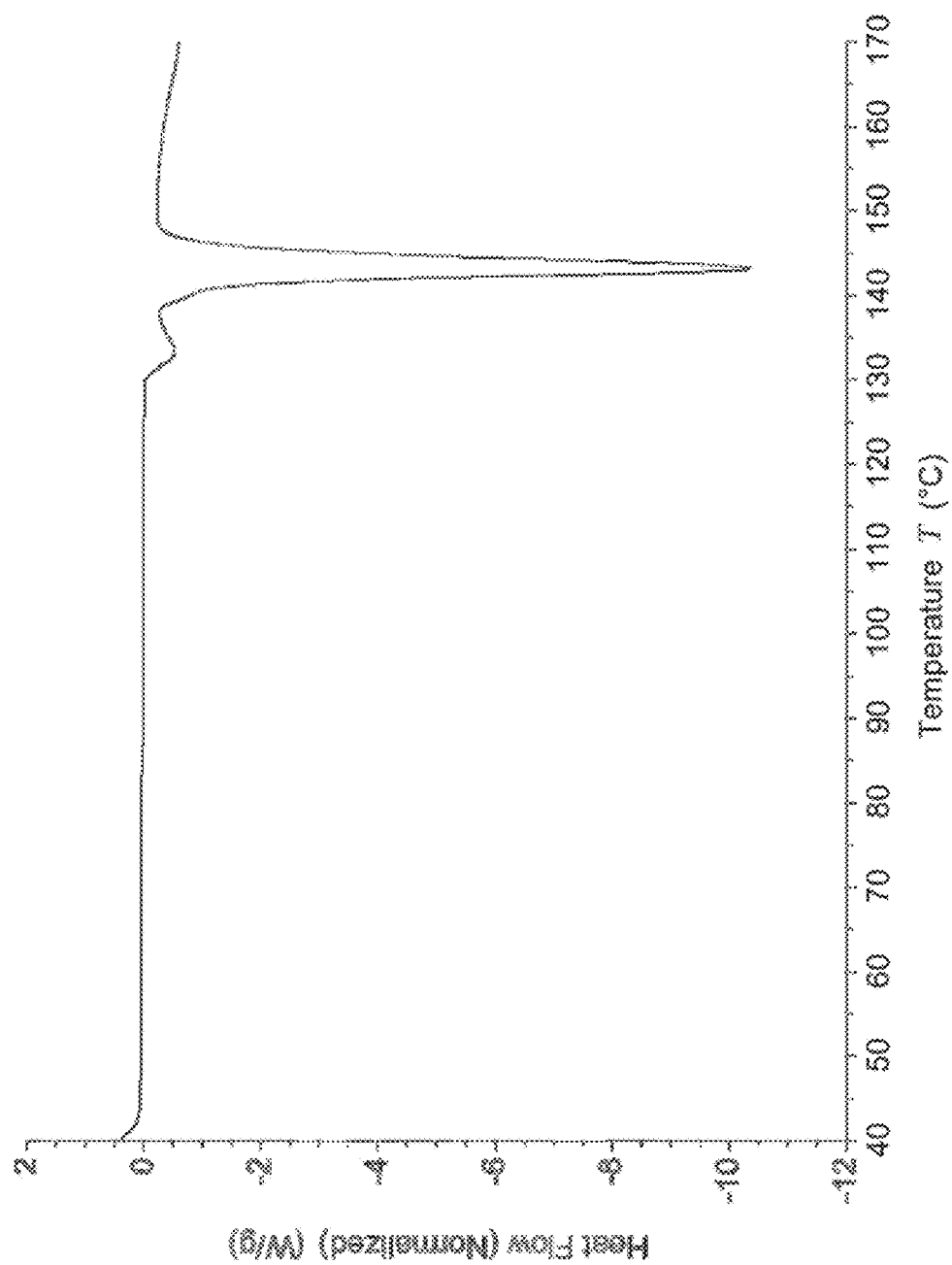
FIG. 16 shows the DSC of N-methylglycine:L-tartaric acid (2:1 co-crystal) from Example 4.
Figure 20:
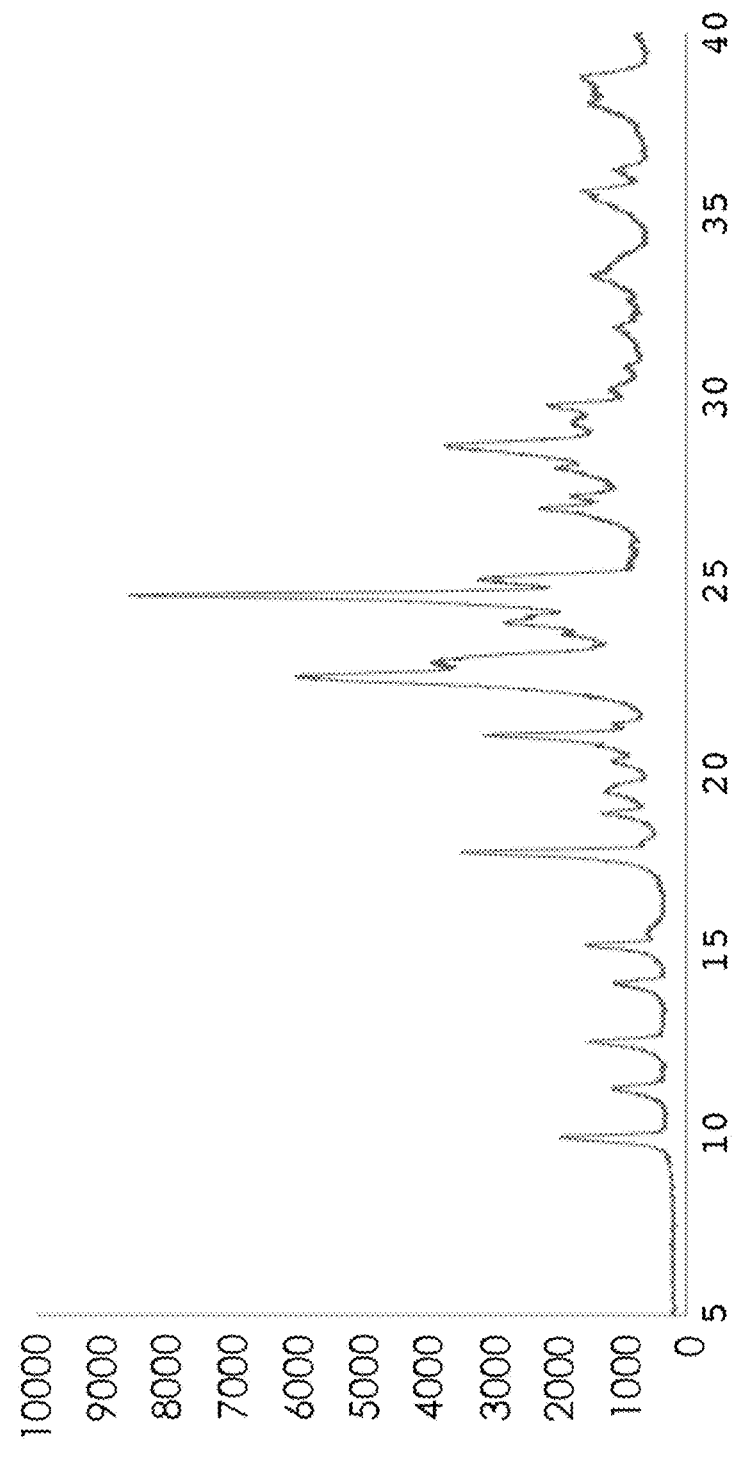
FIG. 20 shows the XRPD of N-methylglycine:fumaric acid (1:1 co-crystal) from Example 11, at a 2θ angle with peaks (°) of: 9.81, 11.10, 12.44, 13.99, 15.05, 17.63, 18.65, 19.20, 20.05, 20.80, 20.94, 22.41, 22.60, 23.51, 23.84, 24.61, 25.01, 26.95, 27.25, 28.07, 28.66, 29.23, 29.75, 30.05, 31.85, 33.23, 33.42, 35.49, 36.12, 37.94, 38.15, and 38.58.
Figure 21:
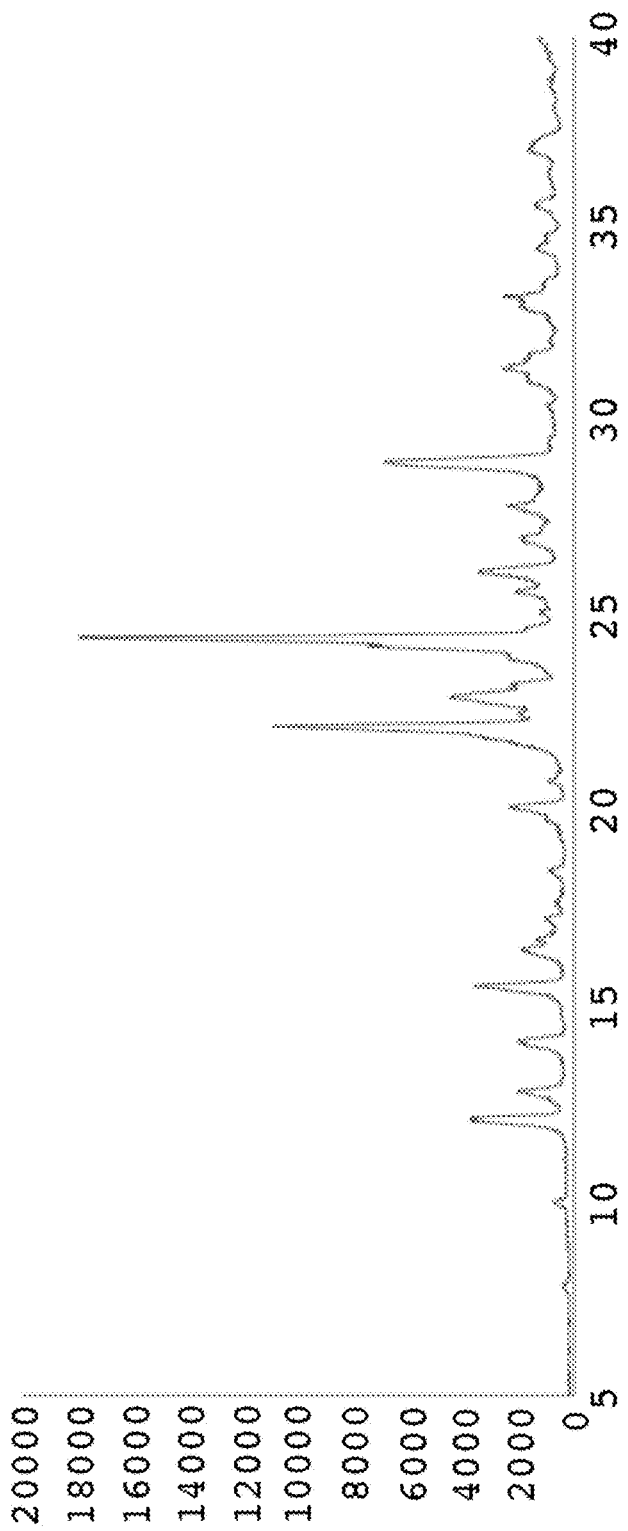
FIG. 21 shows the XRPD of N-methylglycine:fumaric acid (2:1 co-crystal) from Example 11, at a 2θ angle with peaks (°) of: 7.66, 9.89, 12.06, 12.78, 14.00, 15.52, 16.40, 16.58, 17.14, 17.49, 18.42, 19.74, 20.12, 20.75, 22.22, 22.46, 22.93, 23.16, 23.93, 24.29, 24.52, 24.66, 25.32, 25.66, 26.18, 26.98, 27.86, 29.00, 31.06, 31.41, 31.62, 32.96, 33.28, 33.46, 34.45, 34.70, 35.55, and 37.01.
Figure 22:
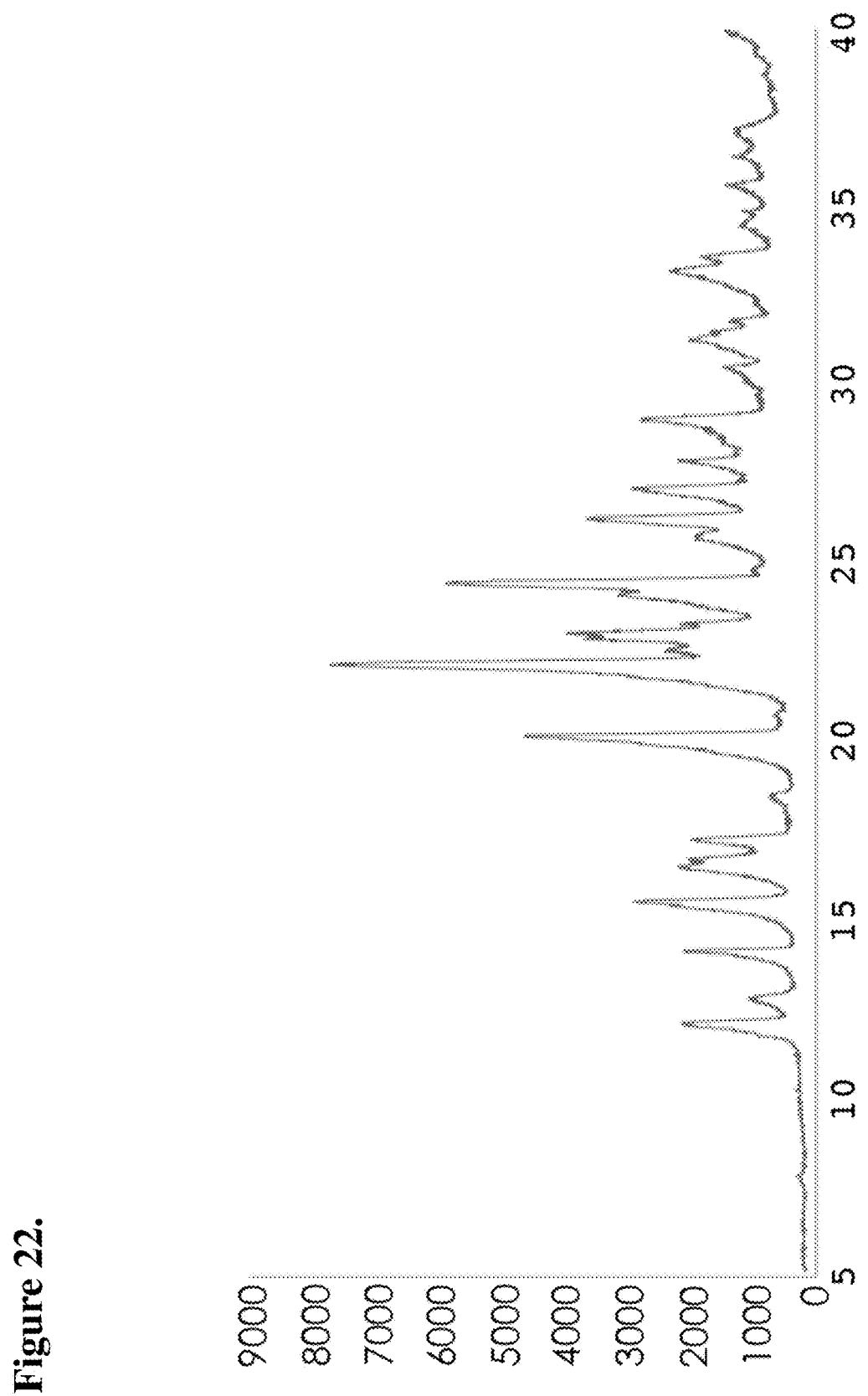
FIG. 22 shows the XRPD of N-methylglycine:fumaric acid (3:1 co-crystal) from Example 11, at a 2θ angle with peaks (°) of: 12.03, 12.70, 14.12, 15.50, 16.42, 16.52, 17.21, 18.29, 20.15, 22.16, 22.35, 22.88, 23.02, 23.17, 24.11, 24.43, 25.66, 26.22, 27.09, 27.87, 28.30, 28.53, 29.00, 30.41, 31.24, 31.38, 31.65, 33.13, 33.42, 34.33, 34.68, 35.55, 36.37, 36.92, and 39.79.
Figure 23:
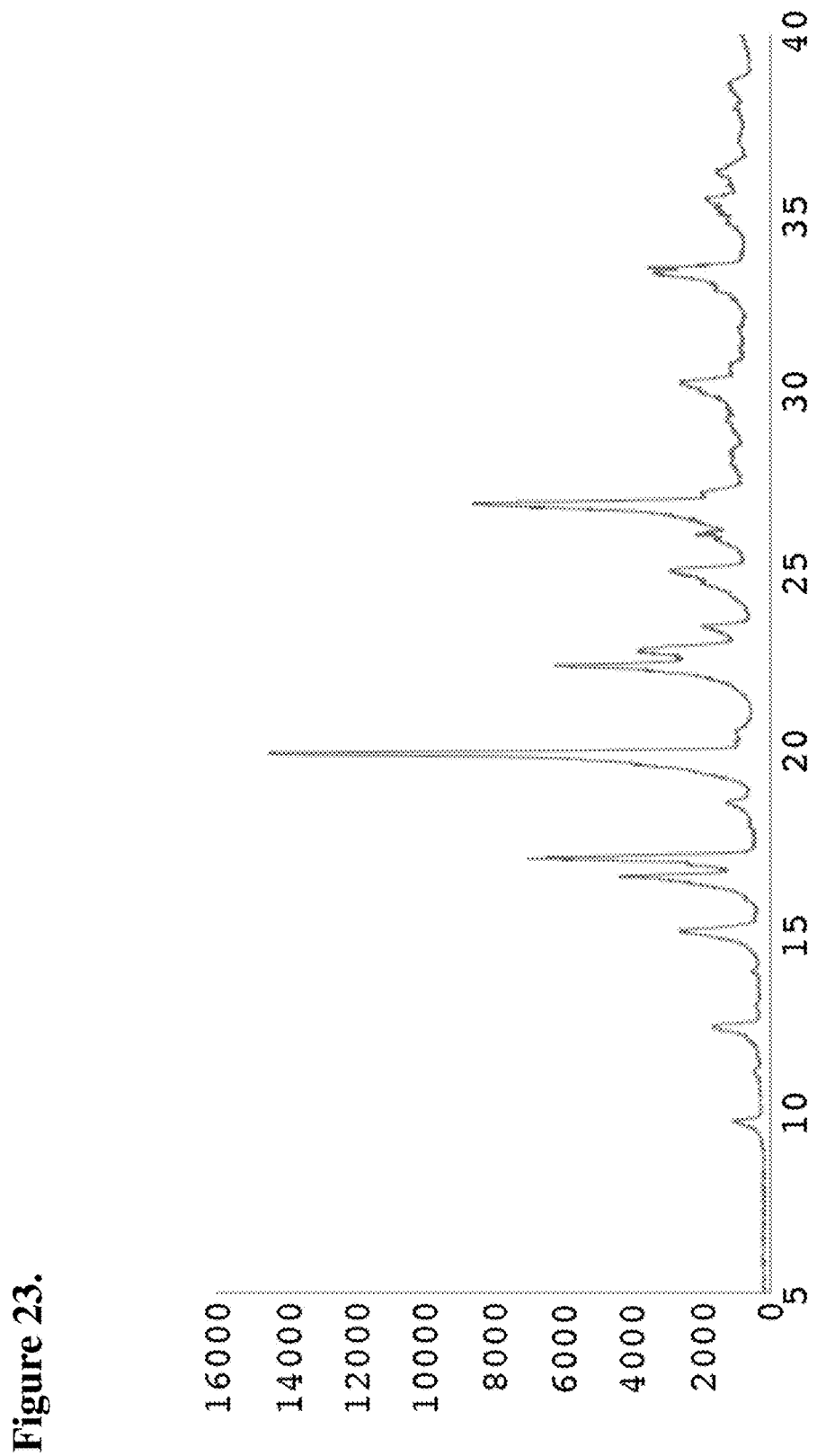
FIG. 23 shows the XRPD of N-methylglycine:fumaric acid (6:1 co-crystal) from Example 11, at a 2θ angle with peaks (°) of: 9.66, 12.30, 15.00, 16.55, 17.07, 18.51, 19.98, 20.39, 22.43, 22.79, 23.43, 24.63, 24.99, 25.84, 26.06, 26.92, 27.11, 27.90, 28.17, 29.05, 29.40, 30.19, 30.49, 32.81, 33.29, 33.34, 34.52, 34.76, 34.97, 35.20, 35.57, 35.99, 37.75, and 38.36.

In some embodiments, the co-crystal has a powder X-ray diffraction pattern substantially as depicted in FIG. 2. In some embodiments, the co-crystal has a powder X-ray diffraction pattern substantially as depicted in FIG. 2, and an endothermic peak corresponding to the melting point of about 140° C. In some embodiments, the endothermic peak corresponds to the melting point of about 140° C. In some embodiments, the co-crystal has a powder X-ray diffraction pattern substantially as depicted in FIG. 2, and an endothermic peak corresponding to the melting point of about 139° C. In some embodiments, the endothermic peak corresponds to the melting point of about 139° C. In some embodiments, the co-crystal has a powder X-ray diffraction pattern substantially as depicted in FIG. 6. In some embodiments, the co-crystal has a powder X-ray diffraction pattern substantially as depicted in FIG. 6, and an endothermic peak corresponding to the melting point of about 138° C. In some embodiments, the endothermic peak corresponds to the melting point of about 138° C. In some embodiments, the co-crystal has a powder X-ray diffraction pattern substantially as depicted in FIG. 10. In some embodiments, the co-crystal has a powder X-ray diffraction pattern substantially as depicted in FIG. 10, and an endothermic peak corresponding to the melting point of about 120° C. In some embodiments, the co-crystal has a powder X-ray diffraction pattern substantially as depicted in FIG. 20. In some embodiments, the co-crystal has a powder X-ray diffraction pattern substantially as depicted in FIG. 21. In some embodiments, the co-crystal has a powder X-ray diffraction pattern substantially as depicted in FIG. 22. In some embodiments, the co-crystal has a powder X-ray diffraction pattern substantially as depicted in FIG. 23.

In some embodiments, in Formula (I), X can be absent. In some embodiments, in Formula (I), X can be absent and either $R_1$ or $R_2$ can be absent, and Y and W can be joined by a single bond. In some embodiments, W can be O. In some embodiments, a co-former compound of Formula (I) is of the Formula (IC):

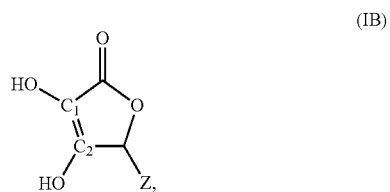

(IB)

wherein $C_1$, $C_2$, and Z are described herein. In some embodiments, the co-former compound is of the formula:

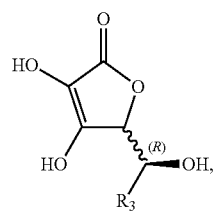

wherein $R_3$ is described herein. In some embodiments, the co-former compound is

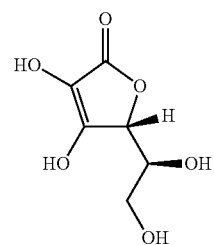 [SMILES: O=C1O[C@H]([C@@H](O)CO)C(O)=C1O]

(erythorbic acid).

In some embodiments, the substituted glycine compound and the co-former of Formula (IB) can exist in the co-crystal in a molecular ratio ranging from 1:0.5 to 1:1.5, but excluding 1:0.5. In some embodiments, the substituted glycine compound and the co-former of Formula (IB) can exist in the co-crystal in a molecular ratio ranging from 1:0.6 to 1:1.4. In some embodiments, the substituted glycine compound and the co-former of Formula (IC) can exist in the co-crystal in a molecular ratio ranging from 1:0.7 to 1:1.3. In some embodiments, the substituted glycine compound and the co-former of Formula (IC) can exist in the co-crystal in a molecular ratio ranging from 1:1 to 1:1.5. In some embodiments, the substituted glycine compound and the co-former of Formula (IC) can exist in the co-crystal in a molecular ratio ranging from 1:1 to 1:1.3. In some embodiments, the substituted glycine compound and the co-former of Formula (IC) can exist in the co-crystal in a molecular ratio ranging from 1:1 to 1:1.2. In some embodiments, the substituted glycine compound and the co-former of Formula (IC) can exist in the co-crystal in a molecular ratio ranging from 1:1 to 1:1.1. In some embodiments, the substituted glycine compound and the co-former of Formula (IC) can exist in the co-crystal in a molecular ratio of 1:1.

Method of Synthesis

In certain embodiments, the synthesis of a co-crystal of substituted glycine and a co-former compound of Formula (I) includes a first step of mixing the substituted glycine compound and a co-former of Formula (I), followed by a step of heating and stirring the solution, a step of cooling and stirring the solution, and a step of collecting the thus formed co-crystal. In certain embodiments, the first step in the synthesis of a co-crystal of substituted glycine and a co-former compound of Formula (I) is a step of mixing substituted glycine compound and the co-former at a temperature of about 40-110° C. to form a saturated solution, wherein the substituted glycine and the co-former are at a molar ratio of 10:1 to 1:10. In certain embodiments, the substituted glycine and the co-former are mixed at a temperature of 40-50° C. to form a saturated solution. In certain embodiments, the substituted glycine and the co-former are mixed at a temperature of 40-60° C. to form a saturated solution. In certain embodiments, the substituted glycine and the co-former are mixed at a temperature of 40-80° C. to form a saturated solution. In certain embodiments, the substituted glycine and the co-former are mixed at a temperature of 40-100° C. to form a saturated solution. In certain embodiments, the substituted glycine and the co-former are mixed at a temperature of 50-110° C. to form a saturated solution. In certain embodiments, the substituted glycine and the co-former are mixed at a temperature of 50-100° C. to form a saturated solution. In certain embodiments, the substituted glycine and the co-former are mixed at a temperature of 60-110° C. to form a saturated solution. In certain embodiments, the substituted glycine and the co-former are mixed at a temperature of 80-110° C. to form a saturated solution. In certain embodiments, the substituted glycine and the co-former are mixed at a temperature of 100-110° C. to form a saturated solution. In some embodiments, the substituted glycine and the co-former are in a molecular ratio ranging from 10:1 to 1:10. In some embodiments, the substituted glycine and the co-former are in a molecular ratio ranging from 8:1 to 1:8. In some embodiments, the substituted glycine and the co-former are in a molecular ratio ranging from 6:1 to 1:6. In some embodiments, the substituted glycine and the co-former are in a molecular ratio ranging from 5:1 to 1:5. In some embodiments, the substituted glycine and the co-former are in a molecular ratio ranging from 4:1 to 1:4. In some embodiments, the substituted glycine and the co-former are in a molecular ratio ranging from 3:1 to 1:3. In some embodiments, the substituted glycine and the co-former are in a molecular ratio ranging from 2:1 to 1:2. In some embodiments, the substituted glycine and the co-former are in a molecular ratio of 1:1.

In certain embodiments, the second step in the synthesis of a co-crystal of substituted glycine and a co-former compound of Formula (I) is a step of heating and stirring the solution at a temperature of about 40-110° C. In certain embodiments, in the second step in the synthesis of a co-crystal, the solution is heated and stirred to a temperature of about 40-110° C. for about 1-10 hours. In certain embodiments, in the second step in the synthesis of a co-crystal, the solution is heated and stirred to a temperature of about 50-110° C. In certain embodiments, in the second step in the synthesis of a co-crystal, the solution is heated and stirred to a temperature of about 60-110° C. In certain embodiments, in the second step in the synthesis of a co-crystal, the solution is heated and stirred to a temperature of about 70-110° C. In certain embodiments, in the second step in the synthesis of a co-crystal, the solution is heated and stirred to a temperature of about 100-110° C. In certain embodiments, the solution is heated and stirred for about 1-5 hours, about 1-10 hours, about 1-15 hours, or about 1-20 hours.

In certain embodiments, the third step in the synthesis of a co-crystal of substituted glycine and a co-former compound of Formula (I) (e.g., Formula IA, IB, or IC) is a step of cooling and stirring the solution to form the co-crystal at a temperature of about 10-30° C. In certain embodiments, in the third step in the synthesis of a co-crystal, the solution is cooled and stirred to a temperature of about 4-30° C. for about 10-36 hours. In certain embodiments, in the third step in the synthesis of a co-crystal, the solution is cooled and stirred to a temperature of about 15-30° C. In certain embodiments, in the third step in the synthesis of a co-crystal, the solution is cooled and stirred to a temperature of about 20-30° C. In certain embodiments, in the third step in the synthesis of a co-crystal, the solution is cooled and stirred to a temperature of about 25° C. In certain embodiments, in the third step in the synthesis of a co-crystal, the solution is cooled and stirred to a temperature of about 4° C., about 5° C., about 10° C., about 15° C., about 20° C., about 25° C., about 30° C., or about 35° C. In certain embodiments, the solution is cooled and stirred for about 5-40 hours, about 5-36 hours, about 5-30 hours, about 10-36 hours, about 10-30 hours, or about 10-25 hours. In certain embodiments, the last step in the synthesis of a co-crystal of substituted glycine and a co-former compound of Formula (I) is a step of collecting the co-crystal formed in the third step.

Any of the co-crystals described herein may be prepared by a method involving heating followed by cooling of saturated solution. One example follows.

In some embodiments, crystallization can be carried out by heating then cooling in a saturated solution. The substituted glycine and co-crystal former can be mixed in a molar ratio of ranging from 10:1 to 1:10 and placed in a round-bottom flask in a water bath at room temperature or elevated temperature (e.g., 60-65° C.). The solvent (e.g., methanol, ethanol, etc.) can be added dropwise via an addition funnel into the flask and the resulting solution was stirred until all powders were fully dissolved. The mixture can be heated and stirred at about 45-55° C. first then cooled and stirred at about 20-25° C., allowing formation of the co-crystal. The co-crystal was collected by suction filtration and could be washed with the mother liquor if necessary before subjecting to drying at room temperature or elevated temperature in the oven overnight.

Compositions

The present disclosure provides compositions comprising a co-crystal described herein, and a carrier. In certain embodiments, the carrier is a pharmaceutically acceptable excipient. In certain embodiments, a composition described herein comprises a co-crystal described herein, and a carrier. The compositions described herein are useful in treating and/or reducing the risk for a neuropsychiatric disorder or a glucose or lipid metabolic disorder.

In certain embodiments, the composition is a pharmaceutical composition. In certain embodiments, the composition is a nutraceutical composition. In certain embodiments, the composition is a health food. In some embodiments, the compositions described herein can be a health food or health food product, which can be any kinds of liquid and solid/ semi-solid materials that are used for nourishing humans and animals, for improving basic behavioral functioning, hyperactivity, anxiety, depression, sensorimotor gating, pain threshold, memory and/or cognitive functioning, or for facilitating treatment of any of the target diseases noted herein (e.g., a neuropsychiatric disorder or a glucose or lipid metabolic disorder, including those described herein). The health food product may be a food product (e.g., tea-based beverages, juice, soft drinks, coffee, milk, jelly, cookies, cereals, chocolates, snack bars, herbal extracts, dairy products (e.g., ice cream, and yogurt)), a food/dietary supplement, or a nutraceutical formulation.

The health food product described herein, may comprise one or more edible carriers, which confer one or more of the benefits to the product as described herein. Examples of edible carriers include starch, cyclodextrin, maltodextrin, methylcellulose, carbonmethoxy cellulose, xanthan gum, and aqueous solutions thereof. Other examples include solvents, dispersion media, coatings, surfactants, antioxidants, preservatives (e.g., antibacterial agents, antifungal agents), isotonic agents, absorption delaying agents, stabilizers, gels, binders, excipients, disintegration agents, lubricants, sweetening agents, flavoring agents, dyes, such like materials and combinations thereof, as would be known to one of ordinary skill in the art. In some examples, the health food products described herein may further include neuroprotective foods, such as fish oil, flax seed oil, and/or benzoate.

In some examples, the health food product is a nutraceutical composition, which refers to compositions containing components from food sources and conferring extra health benefits in addition to the basic nutritional value found in foods. A nutraceutical composition as described herein comprises the co-crystal described herein (e.g., the substituted glycine compound and co-crystal as described herein) and additional ingredients and supplements that promote good health and/or enhance stability and bioactivity of the co-crystals.

The actions of nutraceutical compositions may be fast or/and short-term or may help achieve long-term health objectives as those described herein, e.g., improving basic behavioral functioning, hyperactivity, anxiety, depression, sensorimotor gating, pain threshold, memory and/or cognitive functioning in, e.g., human subjects who have or are at risk for a neuropsychiatric disorder or a glucose or lipid metabolic disorder. The nutraceutical compositions may be contained in an edible material, for example, as a dietary supplement or a pharmaceutical formulation. As a dietary supplement, additional nutrients, such as vitamins, minerals or amino acids may be included. The composition can also be a drink or a food product, e.g., tea, soft drink, juice, milk, coffee, cookie, cereal, chocolate, and snack bar. If desired, the composition can be sweetened by adding a sweetener such as sorbitol, maltitol, hydrogenated glucose syrup and hydrogenated starch hydrolyzate, high fructose corn syrup, cane sugar, beet sugar, pectin, or sucralose.

The nutraceutical composition disclosed herein can be in the form of a solution. For example, the nutraceutical formulation can be provided in a medium, such as a buffer, a solvent, a diluent, an inert carrier, an oil, or a creme. In some examples, the formulation is present in an aqueous solution that optionally contains a non-aqueous co-solvent, such as an alcohol. The nutraceutical composition can also be in the form of powder, paste, jelly, capsule, or tablet. Lactose and corn starch are commonly used as diluents for capsules and as carriers for tablets. Lubricating agents, such as magnesium stearate, are typically added to form tablets.

The health food products may be formulated for a suitable administration route, for example, oral administration. For oral administration, the composition can take the form of, for example, tablets or capsules, prepared by conventional means with acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Also included are bars and other chewable formulations.

In some examples, the health food product can be in a liquid form and the one or more edible carriers can be a solvent or dispersion medium comprising but not limited to, ethanol, polyol (e.g., glycerol, propylene glycol, liquid polyethylene glycol), lipids (e.g., triglycerides, vegetable oils, liposomes) or combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof. In many cases, it will be advisable to include an isotonic agent, such as, for example, sugars, sodium chloride or combinations thereof.

Liquid preparations for oral administration can take the form of, for example, solutions, syrups or suspensions, or they can be presented as a dry product for constitution with water or other suitable vehicle before use. In one embodiment, the liquid preparations can be formulated for administration with fruit juice. Such liquid preparations can be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates, benzoate or sorbate).

In certain embodiments, the composition is a medical food. A medical food product is a food product formulated to be consumed or administered enterally. Such a food product is usually used under the supervision of a physician for the specific dietary management of a target disease, such as those described herein. In some instances, such a medical food composition is specially formulated and processed (as opposed to a naturally occurring foodstuff used in a natural state) for a patient in need of the treatment (e.g., human patients who suffer from illness or who requires use of the product as a major active agent for alleviating a disease or condition via specific dietary management). In some examples, a medical food composition described herein is not one of those that would be simply recommended by a physician as part of an overall diet to manage the symptoms or reduce the risk of a disease or condition.

Any of the medical food compositions described herein, comprising substituted glycine compound and a co-former of Formula (I) thereof and at least one carrier (e.g., those described herein), can be in the form of a liquid solution; powder, bar, wafer, a suspension in an appropriate liquid or in a suitable emulsion, as detailed below. The at least one carrier, which can be either naturally-occurring or synthetic (non-naturally occurring), would confer one or more benefits to the substituted glycine compound and co-former in the composition, for example, stability, bioavailability, and/or bioactivity. Any of the carriers described herein may be used for making the medical food composition. In some embodiments, the medical food composition may further comprise one or more additional ingredients selected from the group including, but not limited to natural flavors, artificial flavors, major trace and ultra-trace minerals, minerals, vitamins, oats, nuts, spices, milk, egg, salt, flour, lecithin, xanthan gum and/or sweetening agents. The medical food composition may be placed in a suitable container, which may further comprise at least an additional therapeutic agent such as those described herein.

In certain embodiments, the co-crystal described herein is provided in an effective amount in the pharmaceutical composition. In certain embodiments, the effective amount is a therapeutically effective amount (e.g., amount effective for treating and/or reducing the risk for a neuropsychiatric disorder or a glucose or lipid metabolic disorder in a subject in need thereof). In certain embodiments, the neuropsychiatric disorder is a neurological disorder, e.g., Alzheimer's disease. In certain embodiments, the glucose or lipid metabolic disorder is obesity. In certain embodiments, the effective amount is a prophylactically effective amount (e.g., amount effective for preventing a neuropsychiatric disorder or a glucose or lipid metabolic disorder in a subject in need thereof).

Pharmaceutical compositions described herein can be prepared by any method known in the art of pharmacology. In general, such preparatory methods include bringing the co-crystal described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the digestive tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the digestive tract, optionally, in a delayed manner. Examples of encapsulating agents which can be used include, but are not limited to, polymeric substances and waxes.

Although the descriptions of pharmaceutical compositions provided herein are mainly directed to pharmaceutical compositions which are suitable for administration to humans, such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

The co-crystals provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

Also encompassed by the disclosure are kits (e.g., pharmaceutical packs). The kits provided may comprise a pharmaceutical composition or co-crystal described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or co-crystal described herein. In some embodiments, the pharmaceutical composition or co-crystal described herein provided in the first container and the second container are combined to form one unit dosage form.

In certain embodiments, a kit described herein includes a first container comprising a co-crystal or composition described herein. In certain embodiments, a kit described herein is useful in treating and/or reducing the risk for a neuropsychiatric disorder in a subject in need thereof or in treating and/or reducing the risk for a glucose or lipid metabolic disorder.

In certain embodiments, a kit described herein further includes instructions for using the co-crystal or composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating and/or reducing the risk for a neuropsychiatric or glucose or lipid metabolic disorder in a subject in need thereof. A kit described herein may include one or more additional pharmaceutical agents described herein as a separate composition.

Methods of Treatment

The present disclosure provides methods of treating and/or reducing the risk for a neuropsychiatric or glucose or lipid metabolic disorder, in a subject in need thereof, the methods comprising administering to the subject an effective amount (e.g., therapeutically effective amount) of a co-crystal, or composition thereof, described herein.

Another aspect of the present disclosure relates to methods of preventing a neuropsychiatric or glucose or lipid metabolic disorder in a subject in need thereof, the methods comprising administering to the subject an effective amount (e.g., prophylactically effective amount) of a co-crystal, or composition thereof, described herein.

The co-crystals and compositions described herein are useful in treating and/or preventing neuropsychiatric or glucose or lipid metabolic disorder. In certain embodiments, the neuropsychiatric disorder is schizophrenia. In certain embodiments, the neuropsychiatric disorder is a psychotic disorder. In certain embodiments, the neuropsychiatric disorder is Alzheimer's disease. In certain embodiments, the neuropsychiatric disorder is frontotemporal dementia. In certain embodiments, the neuropsychiatric disorder is dementia. In certain embodiments, the neuropsychiatric disorder is mild cognitive impairment. In certain embodiments, the neuropsychiatric disorder is benign forgetfulness. In certain embodiments, the neuropsychiatric disorder is closed head injury. In certain embodiments, the neuropsychiatric disorder is autistic spectrum disorder including Asperger's disorder. In certain embodiments, the neuropsychiatric disorder is an attention deficit hyperactivity disorder. In certain embodiments, the neuropsychiatric disorder is obsessive compulsive disorder. In certain embodiments, the neuropsychiatric disorder is a tic disorder. In certain embodiments, the neuropsychiatric disorder is a childhood learning disorder. In certain embodiments, the neuropsychiatric disorder is premenstrual syndrome. In certain embodiments, the neuropsychiatric disorder is depression, including dysthymia and bereavement. In certain embodiments, the neuropsychiatric disorder is suicidal ideation and/or behavior. In certain embodiments, the neuropsychiatric disorder is bipolar disorder including bipolar I and II disorders. In certain embodiments, the neuropsychiatric disorder is an anxiety disorder including panic and phobic disorders. In certain embodiments, the neuropsychiatric disorder is post-traumatic stress disorder. In certain embodiments, the neuropsychiatric disorder is chronic pain. In certain embodiments, the neuropsychiatric disorder is an eating disorder including bulimia and anorexia. In certain embodiments, the neuropsychiatric disorder is an addiction disorder including substance dependence or abuse. In certain embodiments, the neuropsychiatric disorder is a personality disorder. In certain embodiments, the neuropsychiatric disorder is Parkinson's disorder. In certain embodiments, the neuropsychiatric disorder is Huntington's disorder. In certain embodiments, the neuropsychiatric disorder is amyotrophic lateral sclerosis. In certain embodiments, the glucose or lipid metabolic disorder is obesity. In certain embodiments, the glucose or lipid metabolic disorder is diabetes. In certain embodiments, the glucose or lipid metabolic disorder is hypercholesterolemia. In certain embodiments, the glucose or lipid metabolic disorder is hyperlipidemia. In certain embodiments, the glucose or lipid metabolic disorder is hypertension.

In certain embodiments, the method described herein further includes administering to the subject an additional pharmaceutical agent. In certain embodiments, the method described herein further includes contacting the biological sample with an additional pharmaceutical agent. In certain embodiments, the method described herein further includes contacting the tissue with an additional pharmaceutical agent. In certain embodiments, the method described herein further includes contacting the cell with an additional pharmaceutical agent.

The co-crystals and compositions provided herein can be administered by any route, including enteral (e.g., oral), parenteral, intravenous, intramuscular, intra-arterial, intramedullary, intrathecal, subcutaneous, intraventricular, transdermal, interdermal, subcutaneous, intradermal, rectal, intravaginal, intraperitoneal, topical (as by powders, ointments, creams, and/or drops). Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a co-crystal required to achieve an effective amount will vary from subject to subject, depending, for example, on species, age, and general condition of a subject, severity of the side effects or disorder, identity of the particular co-crystal, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a co-crystal described herein. In certain embodiments, when multiple doses are administered to a subject or applied to a biological sample, tissue, or cell, the frequency of administering the multiple doses to the subject or applying the multiple doses to the tissue or cell is three doses a day, two doses a day, one dose a day, one dose every other day, one dose every third day, one dose every week, one dose every other week, one dose monthly or one dose every other month. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, biological sample, tissue, or cell. In certain embodiments, the duration between the first dose and last dose of the multiple doses is three months, six months, or one year. In certain embodiments, the duration between the first dose and last dose of the multiple doses is the lifetime of the subject, biological sample, tissue, or cell. In certain embodiments, a dose (e.g., a single dose, or any dose of multiple doses) described herein includes independently between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a co-crystal described herein. In certain embodiments, a dose described herein includes independently between 3 mg and 10 mg, inclusive, of a co-crystal described herein. In certain embodiments, a dose described herein includes independently between 10 mg and 30 mg, inclusive, of a co-crystal described herein. In certain embodiments, a dose described herein includes independently between 30 mg and 100 mg, inclusive, of a co-crystal described herein. In certain embodiments, a dose described herein includes independently between 100 mg and 300 mg, inclusive, of a co-crystal as described herein. In certain embodiments, a dose described herein includes independently between 300 mg and 1000 mg, inclusive, of a co-crystal described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A co-crystal or composition, as described herein, can be administered in combination with one or more additional pharmaceutical agents (e.g., therapeutically and/or prophylactically active agents) useful in treating and/or reducing the risk for a neuropsychiatric or glucose or lipid metabolic disorder. The co-crystals or compositions can be administered in combination with additional pharmaceutical agents that improve their activity (e.g., activity (e.g., potency and/or efficacy) in treating and/or reducing the risk for a neuropsychiatric or glucose or lipid metabolic disorder in a subject in need thereof), improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including a co-crystal described herein and an additional pharmaceutical agent shows a synergistic effect that is absent in a pharmaceutical composition including one of the co-crystal and the additional pharmaceutical agent, but not both.

The co-crystal or composition can be administered concurrently with, prior to, or subsequent to one or more additional pharmaceutical agents, which may be useful as, e.g., combination therapies in treating and/or reducing the risk for a neuropsychiatric or glucose or lipid metabolic disorder in a subject. Pharmaceutical agents include therapeutically active agents. Pharmaceutical agents also include prophylactically active agents. Pharmaceutical agents include small organic molecules such as drug compounds or co-crystals thereof (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, antibodies, small molecules linked to proteins such as antibodies, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful in treating and/or reducing the risk for a neuropsychiatric or glucose or lipid metabolic disorder in a subject. In certain embodiments, the additional pharmaceutical agent is a pharmaceutical agent approved by a regulatory agency (e.g., the US FDA) for treating and/or reducing the risk for a neuropsychiatric or glucose or lipid metabolic disorder in a subject. Each additional pharmaceutical agent may be administered at a dose and/or on a time schedule determined for that pharmaceutical agent. The additional pharmaceutical agents may also be administered together with each other and/or with the co-crystal or composition described herein in a single dose or administered separately in different doses. The particular combination to employ in a regimen will take into account compatibility of the co-crystal described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

In certain embodiments, the additional pharmaceutical agent is an agent for treating and/or reducing the risk for a neuropsychiatric disorder, an agent for treating and/or reducing the risk for a glucose or lipid metabolic disorder, or a combination thereof. In certain embodiments, the co-crystals described herein or pharmaceutical compositions can be administered in combination with a therapy for treating and/or reducing the risk for a neuropsychiatric disorder or a glucose or lipid metabolic disorder.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

In order that the present disclosure may be more fully understood, the following examples are set forth. The synthetic and biological examples described in this application are offered to illustrate the co-crystals, compounds, compositions, and methods provided herein and are not to be construed in any way as limiting their scope.

The following are exemplary methods of preparing co-crystals described herein.

Example 1: Preparation of N-Methylglycine:D-Tartaric Acid (1:1 Co-Crystal) Via Heating Followed by Cooling in Saturated Solution N-methylglycine (5.0 g, 56.1 mmol) and D-tartaric acid (10.1 g, 67.3 mmol) were placed in 62 mL of methanol and stirred at 50° C. until all reagents were dissolved to form a solution. The solution was further stirred at 50° C. for 5 hours, then cooled to room temperature overnight to allow precipitation of solids. After the precipitation ceased, the solution was filtered and the solids collected were dried under vacuum at room temperature for 24 hours to give 11.0 g of N-methylglycine:D-tartaric acid (1:1) co-crystal. The co-crystal thus obtained was analyzed by $^1$H-NMR, powder X-ray diffraction, and thermoanalysis as described herein.

Thermogravimetric Analysis (TGA):

TGA data were measured by Pyris 1 TGA (Perkin Elmer) with platinum crucibles with the heating rate of 10° C./min, between 50° C.–700° C.

Differential Scanning Calorimetry:

The melting point of the co-crystal was determined using the differential scanning calorimeter (DSC) method. The DSC data were measured by DSC 25 (TA Instruments) with T-zero aluminum low-mass pan at the heating rate of 10° C./min and the heating range of 40° C.–230° C.

X-ray Powder Diffractometry (XRPD):

X-ray diffraction patterns were obtained on D8 ADVANCE (Bruker AXS Gmbh, Germany). Samples were scanned in continuous mode from 0-45° (2θ) with step size of 0.02° on a spinning stage at 40 kV and 40 mA with Cu Kα radiation.

The incident beam path was equipped with a 0.2 mm divergence slit and 0.02 mm air scattering screen. The diffracted beam was equipped with Ni-filter. Detection was accomplished with a Lynxeye detector (Bruker AXS).

$^1$H-NMR:

$^1$H Nuclear magnetic resonance (NMR) analysis was performed on Bruker Fourier 400 (Bruker) in deuterated solvents such as d-methanol or D$_2$O at 25° C. The NMR's for FIGS. 1, 5, 9, and 13 were performed in D$_2$O at 25° C.

The $^1$H-NMR, powder X-ray diffraction, and thermoanalysis results of the co-crystal obtained by the method described in Example 1 are shown in FIGS. 1-4, respectively.

Example 2: Preparation of N-Methylglycine:L-Tartaric Acid (1:1 Co-Crystal) Via Heating Followed by Cooling in Saturated Solution N-methylglycine (5.0 g, 56.1 mmol) and L-tartaric acid (10.1 g, 67.3 mmol) were added into 62 mL of methanol and the resulting slurry was stirred at 50° C. until all reagents were dissolved. The mixture was stirred at 50° C. for 5 hours, and cooled to room temperature overnight for precipitation of solids. The solids were then collected by filtration and dried under vacuum at room temperature for 24 hours to afford 11.0 g of N-methylglycine:L-tartaric acid (1:1) co-crystal. The $^1$H-NMR, powder X-ray diffraction, and thermoanalysis results of the co-crystal obtained by the method described in Example 2 above are shown in FIGS. 5-8, respectively.

Example 3: Preparation of N-Methylglycine:DL-Tartaric Acid (1:1 Co-Crystal) Via Heating Followed Cooling in Saturated Solution To 75 mL of methanol were added N-methylglycine (5.0 g, 56.1 mmol) and DL-tartaric acid (12.6 g, 84.0 mmol) at 50° C. and the mixture was stirred until all reagents were dissolved. The solution thus formed was further stirred at 50° C. for 5 hours, then cooled to room temperature overnight to let the solids to generate. The solids were isolated by filtration and dried by vacuum at room temperature for 24 hours to provide 10 g of N-methylglycine:DL-tartaric acid 1:1 co-crystal. The $^1$H-NMR, powder X-ray diffraction, and thermoanalysis results of the co-crystal obtained by the method described in Example 3 above are shown in FIGS. 9-12, respectively.

Example 4: Preparation of N-Methylglycine:L-Tartaric Acid (2:1 Co-Crystal)

N-methylglycine (25.0 g, 280.6 mmol) and L-tartaric acid (21.0 g, 139.9 mmol) were added to 140 mL of 60% ethanol/water. The mixture was stirred at 40° C. until all reagents were dissolved, and cooled to 30° C. for the addition of seed crystals. The mixture was further cooled to 4° C. followed by the 420 mL of ethanol, and the resulting solution was stirred overnight. The solution was allowed to return to 25° C. and further stirred overnight. The solids formed were collected by filtration and dried under vacuum at room temperature for 24 hours to give N-methylglycine:L-tartaric acid 2:1 co-crystal. The co-crystal obtained was subjected to $^1$H-NMR, powder X-ray diffraction, and thermoanalysis, as shown in FIGS. 13-16.

Example 5: Hygroscopicity Test of N-Methylglycine:L-Tartaric Acid (1:1 Co-Crystal) Vs. N-Methylglycine:L-Tartaric Acid (2:1 Co-Crystal)—Condition 1

Figure 17:
FIGS. 17A-B show the hygroscopicity of N-methylglycine:L-tartaric acid (1:1 co-crystal, FIG. 17A) and N-methylglycine:L-tartaric acid (2:1 co-crystal, FIG. 17B), from Example 5.
Figure 17:
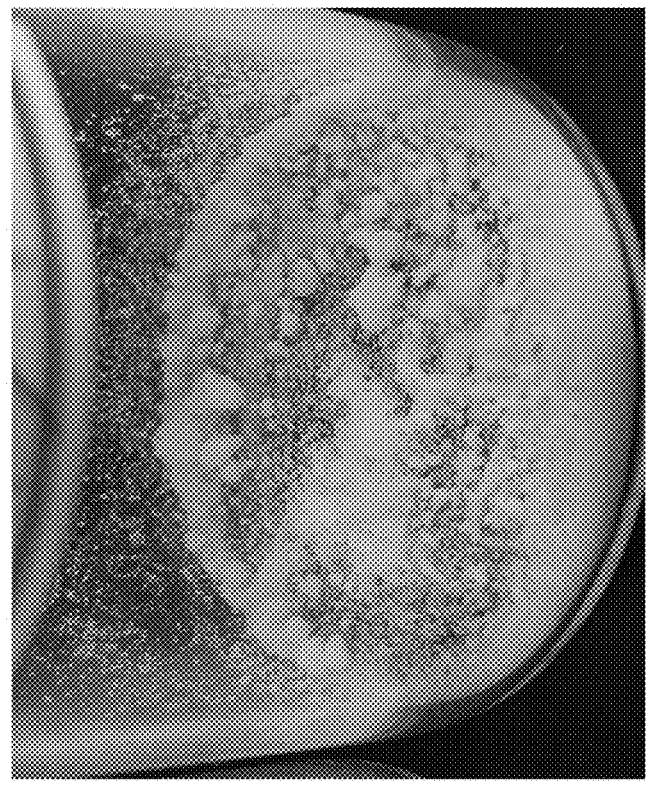

100 mg of each of N-methylglycine:L-tartaric acid (1:1 co-crystal) and N-methylglycine:L-tartaric acid (2:1 co-crystal) was exposed to high humidity condition (70-75% RH) at room temperature for 3 days. The result showed that the 1:1 co-crystal remained as fine white powder while the 2:1 co-crystal turned into moisturized and somewhat sticky white solid. FIGS. 17A-B. This demonstrates that the 1:1 co-crystal is much less hygroscopic than the 2:1 co-crystal.

Example 6: Hygroscopicity Tests of N-Methyglycine:Tartaric Acid Co-Crystals—Condition 2

100-150 mg of each of N-methylglycine:L-tartaric acid 1:1 co-crystal, N-methylglycine:DL-tartaric acid 1:1 co-crystal, N-methylglycine:L-tartaric acid 2:1 co-crystal, N-methylglycine:DL-tartaric acid 2:1 co-crystal, and N-methylglycine was weighed and then placed in the vial under the condition of 30° C. and 75% RH in a humidity chamber. The weight changes at 1 hr, 2 hr, 3 hr, 5 hr, 24 hr, 48 hr, and 72 hr of each co-crystal were measured and illustrated in Table 1 below.

TABLE 1

Hygroscopicity Tests of Various N-Methylglycine:Tartaric Acid Co-Crystals

| Time (hr) | A. N-MG/L-TA = 1/1 Outward | Weight (g) | B. N-MG/DL-TA = 1/1 Outward | Weight (g) | C. N-MG/L-TA = 2/1 Outward | Weight (g) | D. N-MB-DL-TA = 2/1 Outward | Weight (g) | E. N-MG Outward | Weight (g) |
|---|---|---|---|---|---|---|---|---|---|---|
| Dry before | White powder | 0.1434 (+0.1%) | White powder | 0.1305 (+0.2%) | White powder | 0.1457 (+0.1%) | White powder | 0.1628 (+0%) | White powder | 0.1375 (+0%) |
| 0 | | 0.1432 | | 0.1302 | | 0.1455 | | 0.1628 | | 0.1375 |
| 1 | | 0.1437 (+0.3%) | | 0.1349 (+3.6%) | | 0.1462 (+0.4%) | | 0.1695 (+4.3%) | 90% Liquid | 0.1585 (+15.3%) |
| 2 | | 0.1437 (+0.3%) | Wet solid | 0.1399 (+7.4%) | | 0.1463 (+0.5%) | Wet solid | 0.1768 (+8.6%) | | 0.1942 (+41.2%) |
| 3 | | 0.1439 (+0.4%) | | 0.1469 (+12.8%) | | 0.1464 (+0.6%) | | 0.1816 (+11.3%) | Liquid | 0.2146 (+56.1%) |
| 5 | | 0.1439 (+0.4%) | Partial liquid | 0.1545 (+18.7%) | | 0.1465 (+0.7%) | Partial liquid | 0.1877 (+15.3%) | | 0.2403 (+74.8%) |
| 24 | | 0.1440 (+0.5%) | 50% Liquid | 0.1819 (+39.7%) | | 0.1465 (+0.7%) | Liquid | 0.2374 (+45.8%) | | 0.2884 (+109.7%) |
| 48 | | 0.1440 (+0.5%) | | 0.1819 (+39.7%) | | 0.1465 (+0.7%) | | 0.2423 (+48.8%) | | 0.2885 (+109.8%) |
| 72 | | 0.1441 (+0.6%) | | 0.1823 (+40.0%) | Parital liquid | 0.1471 (+1.3%) | | 0.2441 (+49.9%) | | 0.2885 (+109.8%) |

Figure 18:
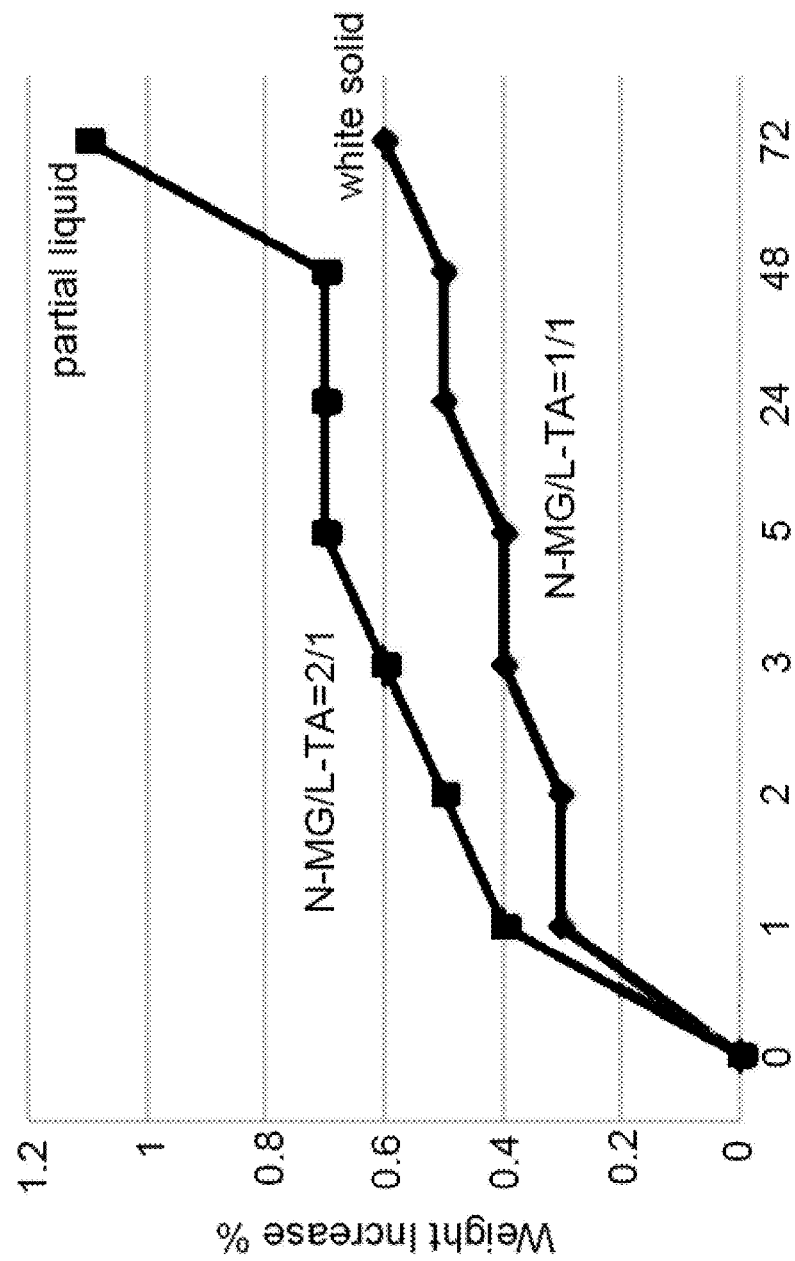
FIG. 18 shows the hygroscopicity of N-methylglycine:L-tartaric acid (1:1 co-crystal) and N-methylglycine:L-tartaric acid (2:1), from Example 6.

The results above indicated that, after 72 hr, the 1:1 N-methylglycine:L-tartaric acid co-crystal absorbed only 0.6% of water and remained as white powder while the 2:1 N-methylglycine:L-tartaric acid co-crystal absorbed 1.1% of water and turned into a partial liquid, showing 1:1 co-crystal is significantly better than 2:1 co-crystal in hygroscopicity, as demonstrated in FIG. 18. In summary, 1:1 N-methylglycine:tartaric acid co-crystal is much less hygroscopic than 2:1 N-methylglycine:tartaric acid co-crystal; 1:1 N-methylglycine:L-tartaric acid co-crystal is much less hygroscopic than 2:1 N-methylglycine:L-tartaric acid co-crystal while 1:1 N-methylglycine:DL-tartaric acid co-crystal is much less hygroscopic than 2:1 N-methylglycine:DL-tartaric acid co-crystal.

Moreover, after 5 hr, the 1:1 N-methylglycine:DL-tartaric acid co-crystal absorbed 18.7% of water and started to turn into a partial liquid, while the N-methylglycine:L-tartaric acid co-crystal absorbed only 0.4% of water showing that the co-crystal of N-methylglycine with the co-former in the single enantiomeric form, D- or L-tartaric acid, was less hygroscopic than that with the co-former in the racemic form, namely, DL-tartaric acid.

Example 7: Hygroscopicity Tests of N-Methyglycine:Tartaric Acid 2:1 Co-Crystals—Condition 3

The hygroscopicity of each of N-methylglycine, N-methylglycine:DL-tartaric acid 2:1 co-crystal, N-methylglycine:D-tartaric acid 2:1 co-crystal, and N-methylglycine:L-tartaric acid 2:1 co-crystal was determined by dynamic vapor sorption on the DVS Advantage (Surface Measurement Systems Ltd., London) for comparison. Measurement were taken from 0 to 90 to 0% RH at 25° C. with 10% RH per step with equilibration set to dm/dt+0.01%/min for 10 min or 180 min/step. All samples reached equilibration at each step before the 180 min maximum set point was reached. The results are summarized in Table 2 below.

TABLE 2

Hygroscopicity Tests of N-Methylglycine:Tartaric Acid 2:1 Co-Crystals

| | | Change In Mass (%) | | |
|---|---|---|---|---|
| RH (%) | N-MG | N-MG/DL-TA = 2/1 | N-MG/D-TA = 2/1 | N-MG/L-TA = 2/1 |
| 0 | 0.0 | 0.00 | 0.00 | 0.00 |
| 10 | 0.0 | 0.15 | 0.02 | 0.01 |
| 20 | 0.0 | 0.21 | 0.04 | 0.03 |
| 30 | 0.0 | 0.26 | 0.07 | 0.05 |
| 40 | 0.0 | 0.77 | 0.10 | 0.07 |
| 50 | 0.0 | 1.25 | 0.15 | 0.09 |
| 60 | 0.0 | 2.03 | 0.20 | 0.13 |
| 70 | 38.6 | 3.12 | 0.31 | 0.18 |
| 80 | 87.4 | 8.12 | 0.60 | 0.32 |
| 90 | 130.9 | 30.35 | 14.27 | 10.74 |

The results above showed that, when the RH was raised to 70%, the N-methylglycine:D-tartaric acid 2:1 co-crystal and N-methylglycine:L-tartaric acid 2:1 co-crystal absorbed only 0.31% and 0.18% of water, respectively, compared to 3.12% for N-methylglycine:DL-tartaric acid 2:1 co-crystal. At 90%, N-methylglycine:L-tartaric acid 2:1 co-crystal absorbed 10.74% of moisture, compared to 14.27% and 30.35% for the 2:1 D-tartaric acid and DL-tartaric acid co-crystals. In summary, the co-crystal of N-methylglycine with L-tartaric acid was the least hygroscopic compared to that with D-tartaric acid and DL-tartaric acid. At the same time, L-tartaric acid co-crystal was much less hygroscopic than the D-tartaric acid co-crystal.

Example 8: Hygroscopicity Tests of N-Methylglycine, L-Tartaric Acid, and N-Methyglycine:L-Tartaric Acid 1:1 Co-Crystal—Condition 4

Figure 19:
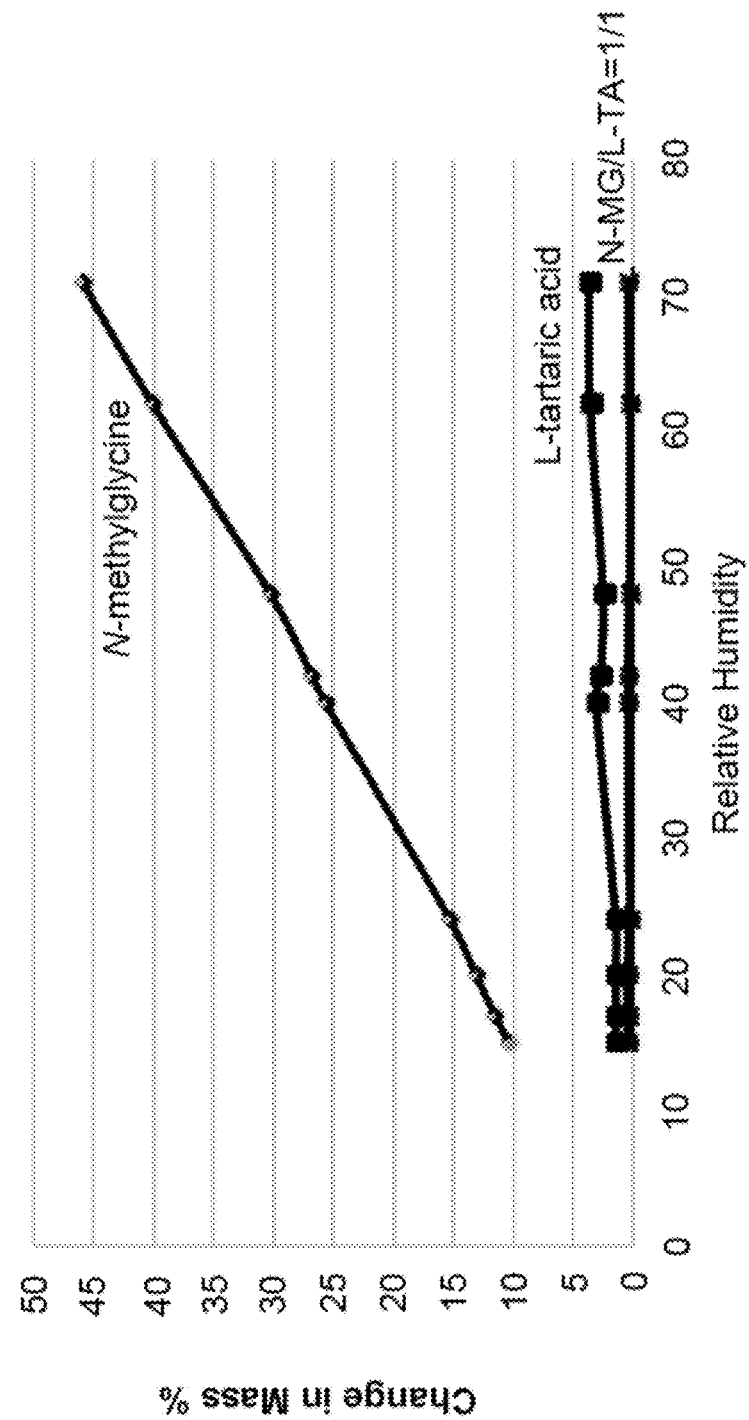
FIG. 19 shows the hygroscopicity of N-methylglycine, L-tartaric acid, and N-methylglycine:L-tartaric acid (1:1 co-crystal), from Example 8.

The hygroscopicity of each of N-methylglycine, L-tartaric acid, and N-methylglycine:L-tartaric acid 1:1 co-crystal, was determined by dynamic vapor sorption on the DVS Advantage (Surface Measurement Systems Ltd., London) for comparison. Measurement were taken from 0 to 70 to 0% RH at 25° C. with 10% RH per step with equilibration set to dm/dt+0.01%/min for 10 min or 180 min/step. All samples reached equilibration at each step before the 180 min maximum set point was reached. The results illustrated that the N-methylglycine:L-tartaric acid 1:1 co-crystal was less hygroscopic than N-methylglycine or L-tartaric acid individually, as shown in FIG. 19.

Example 9: Melting Points of N-Methylglycine and Tartaric Acid Co-Crystals

The melting point of each of the 1:1 and 2:1 co-crystal of N-methylglycine with L-tartaric acid, D-tartaric acid, and DL-tartaric acid was determined by the DSC method and illustrated in Table 3. It was evident that the 1:1 and 2:1 co-crystals of N-methylglycine with the co-former in the single enantiomeric form, D- or L-tartaric acid showed higher melting points than those with the co-former in the racemic form, i.e., DL-tartaric acid, thus more stable under thermal stress at elevated temperatures.

TABLE 3

Melting Points of N-Methylglycine and Tartaric Acid Co-Crystals

| | N-MG/L-TA = 1/1 | N-MG/D-TA = 1/1 | N-MG/DL-TA = 1/1 |
|---|---|---|---|
| Melting Point | 138° C. | 139° C. | 120° C. |
| | N-MG/L-TA = 2/1 | N-MG/D-TA = 2/1 | N-MG/DL-TA = 2/1 |
| Melting Point | 143° C. | 141° C. | 120° C. |

Example 10: Solubilities of N-Methylglycine and Tartaric Acid Co-Crystals Vs. N-Methylglycine in Water 0.1 to 1.0 g of each sample was weighed followed by gradual addition of water to determine the maximum solubility. It was found that the solubilities of 1:1 and 2:1 co-crystals of N-methylglycine with L-tartaric acid are 1250 g/L and 1121 g/L, respectively, higher than that of N-methylglycine of 660 g/L. It was also noted that the 1:1 co-crystal showed higher water solubility than the 2:1 co-crystal, yet less hygroscopicity as shown in Examples 5 and 6.

Example 11: Preparation of N-Methylglycine and Fumaric Acid Co-Crystals

Various ratios (1:1, 2:1, 3:1, and 6:1) of N-methylglycine and fumaric acid co-crystals were prepared by dissolving N-methylglycine and fumaric acid with the corresponding ratios in ethanol followed by the procedures described in Example 1. The XRPD of the 1:1, 2:1, 3:1, and 6:1 co-crystals are shown in Figures, 20, 21, 22, and 23.

Example 12: Hygroscopicity Tests of N-Methylglycine and Fumaric Acid Co-Crystals 0.1 to 0.5 g of each of 1:1, 2:1, 3:1, and 6:1 N-methylglycine co-crystals were placed in the vial under the ambient conditions. The weight changes at various time points of each co-crystal were measured and illustrated in Table 4 below.

TABLE 4

Hygroscopicity Tests of N-Methylglycine Fumaric Acid Co-Crystals

| | Change In Mass (%) | | | |
|---|---|---|---|---|
| Time (hr) | N-MG/FA = 1/1 | N-MG/FA = 2/1 | N-MG/FA = 3/1 | N-MG/FA = 6/1 |
| 1 | 0.48 | — | — | — |
| 2 | 0.67 | — | — | — |
| 3 | 0.57 | — | — | — |
| 4 | 0.57 | — | — | — |
| 5 | 0.57 | — | — | — |
| 15 | — | 5.81 | 18.29 | 18.30 |
| 21 | 0.96 | 6.29 | 20.78 | 25.14 |
| 24 | 0.96 | — | — | — |
| 45 | 0.96 | 7.08 | 26.13 | 47.59 |
| 48 | 0.96 | 7.12 | 26.37 | 48.84 |
| 64 | — | 7.49 | 29.22 | 56.36 |
| 96 | 0.96 | — | — | — |

The results above also suggested that the 1:1 co-crystal of N-methylglycine with fumaric acid was much less hygroscopic than the 2:1, 3:1, and 6:1 co-crystals, similar to the findings in Examples 5 and 6.

EQUIVALENTS AND SCOPE

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A co-crystal of N-methyglycine and tartaric acid, wherein the molecular ratio between the N-methyglycine and the tartaric acid in the co-crystal is 2:1.

2. The co-crystal of claim 1, wherein the tartaric acid is D-tartaric acid.

3. The co-crystal of claim 1, wherein the tartaric acid is L-tartaric acid.

4. The co-crystal of claim 1, wherein the tartaric acid is a racemic mixture of D-tartaric acid and L-tartaric acid.

5. The co-crystal of claim 1, wherein the co-crystal has a powder X-ray diffraction pattern at a 2θ angle with peaks (°) of: 8.1, 10.0, 11.9, 12.7, 13.3, 13.7, 15.5, 15.9, 16.3, 16.7, 17.8, 18.9, 19.8, 20.1, 21.2, 22.1, 24.0, 24.7, 25.0, 25.9, 26.2, 27.6, 28.0, 28.6, 29.4, 29.9, 30.1, 30.2, 30.6, 31.3, 31.8, 31.9, 32.2, 32.6, 33.4, 33.8, 34.7, 35.8, 36.4, 37.0, 38.8, 39.2, 39.7, 39.9, 40.2, 41.1, 41.5, 41.8, 41.9, 42.0, 42.8, 42.9, 43.1, 44.0, 44.1, and 44.5.

6. The co-crystal of claim 1, wherein the co-crystal has a melting point of about 143° C.

7. The co-crystal of claim 1, wherein the co-crystal is produced in a non-aqueous solvent selected from the group consisting of methanol, ethanol, acetic acid, dimethyl sulfoxide, tetrahydrofuran, and diethyl ether.

8. A composition, comprising an effective amount of the co-crystal of claim 1 and a carrier, wherein the composition is formulated in a solid dosage form or a gel form.

9. The composition of claim 8, wherein the composition is a pharmaceutical composition, a nutraceutical composition, a health food, or a medical food.

10. A method of treating or reducing the risk for a neuropsychiatric disorder in a subject, the method comprising administering to a subject in need thereof a therapeutically effective amount of the co-crystal of claim 1.

11. The method of claim 10, wherein the neuropsychiatric disorder is selected from the group consisting of schizophrenia, psychotic disorders, Alzheimer's disease, dementia, frontotemporal dementia, mild cognitive impairment, benign forgetfulness, closed head injury, an autistic spectrum disorder, Asperger's disorder, attention deficit hyperactivity disorders, obsessive compulsive disorder, tic disorders, childhood learning disorders, premenstrual syndrome, depressions, suicidal ideation and/or behavior, bipolar disorders, anxiety disorders, post-traumatic stress disorder, chronic pain, eating disorders, addiction disorders, personality disorders, Parkinson's disorder, Huntington's disorder, and amyotrophic lateral sclerosis.

12. A method for preparing a co-crystal of claim 1, the method comprising:
   (i) mixing the N-methyglycine and the tartaric acid at a molar ratio of 2:1 to 10:1 in a solvent at a temperature of about 40-110° C. to form a solution;
   (ii) cooling the solution at a temperature of about 15-30° C.;
   (iii) further cooling the solution to 4-10° C. for 10-36 hours to allow the formation of the co-crystal; and
   (iv) collecting the co-crystal formed in (iii),
wherein the solvent is a mixture of water and one or more non-aqueous solvents selected from the group consisting of methanol, ethanol, acetic acid, dimethyl sulfoxide, tetrahydrofuran, and diethyl ether.

13. The method of claim 12, further comprising after step (ii) and before step (iii), adding additional seed crystals.

14. The method of claim 12, wherein in step (i), the N-methyglycine and the tartaric acid are at a molar ratio of 2:1 to 6:1.

15. The method of claim 12, wherein step (i) comprises mixing the N-methyglycine and the tartaric acid at a temperature of about 40-80° C.

16. The method of claim 12, wherein step (ii) comprises cooling the solution at a temperature of about 20-30° C.

17. The method of claim 12, wherein step (iii) comprises further cooling the solution at a temperature of about 4° C.

18. The method of claim 12, wherein the solvent is a mixture of water and ethanol.

19. The co-crystal of claim 1, wherein the co-crystal has a melting point of about 120° C.

20. The co-crystal of claim 1, wherein the co-crystal has a melting point of about 141° C.

* * * * *